(12) United States Patent
Akahane et al.

(10) Patent No.: US 9,191,591 B2
(45) Date of Patent: Nov. 17, 2015

(54) IMAGING DEVICE, ENDOSCOPE SYSTEM AND METHOD OF ELIMINATING NOISE

(71) Applicant: OLYMPUS MEDICAL SYSTEMS CORP., Tokyo (JP)

(72) Inventors: Nana Akahane, Hachioji (JP); Makoto Ono, Sagamihara (JP); Takahiro Nishiwaki, Tsukuba (JP); Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 7 days.

(21) Appl. No.: 14/273,696

(22) Filed: May 9, 2014

(65) Prior Publication Data

US 2014/0320618 A1 Oct. 30, 2014

Related U.S. Application Data

(63) Continuation of application No. PCT/JP2013/079009, filed on Oct. 25, 2013.

(30) Foreign Application Priority Data

Jan. 23, 2013 (JP) ................. 2013-010540

(51) Int. Cl.
| | |
|---|---|
| *A61B 1/05* | (2006.01) |
| *H04N 5/363* | (2011.01) |
| *H04N 5/357* | (2011.01) |
| *H04N 5/374* | (2011.01) |
| *H04N 5/378* | (2011.01) |
| *A61B 1/00* | (2006.01) |
| *A61B 1/04* | (2006.01) |
| *H01L 27/146* | (2006.01) |

(52) U.S. Cl.
CPC ............ *H04N 5/363* (2013.01); *A61B 1/00009* (2013.01); *A61B 1/00018* (2013.01); *H04N 5/357* (2013.01); *H04N 5/374* (2013.01); *H04N 5/378* (2013.01); *H04N 5/3741* (2013.01); *A61B 1/04* (2013.01); *H01L 27/14643* (2013.01)

(58) Field of Classification Search
USPC ..................................... 348/65, 305
See application file for complete search history.

(56) References Cited

U.S. PATENT DOCUMENTS

7,352,400 B2 * 4/2008 Sakurai et al. ................. 348/308

FOREIGN PATENT DOCUMENTS

| JP | 5-207220 A | | 8/1993 | |
|---|---|---|---|---|
| JP | 2000-59691 A | | 2/2000 | |
| JP | 2001-257938 A | | 9/2001 | |
| JP | 2001257938 A | * | 9/2001 | ............ H04N 5/335 |
| JP | 2003-198949 A | | 7/2003 | |
| JP | 2004-282236 A | | 10/2004 | |
| JP | 2004282236 A | * | 10/2004 | ............ H04N 5/335 |

OTHER PUBLICATIONS

Decision of a Patent Grant dated Jul. 15, 2014 from related Japanese Application No. 2014-520429, together with an English language translation.

* cited by examiner

*Primary Examiner* — Dave Czekaj
*Assistant Examiner* — Shanika Brumfield
(74) *Attorney, Agent, or Firm* — Scully, Scott, Murphy & Presser, PC

(57) ABSTRACT

An imaging device causes a signal to be output from a first transfer line via a second transfer unit by a noise signal reading operation and a light-noise sum signal reading operation, the noise signal reading operation resetting a transfer capacitor when a signal of a charge converter is output to the first transfer line after a first transfer unit is turned into an OFF state and the charge converter is reset, and the light-noise sum signal reading operation outputting the signal of the charge converter to the first transfer line after the transfer capacitor resetting unit is turned into an OFF state, the first transfer unit is turned into an ON state, and a charge accumulated by a photoelectric conversion element is transferred.

11 Claims, 14 Drawing Sheets

IMAGING DEVICE, ENDOSCOPE SYSTEM AND METHOD OF ELIMINATING NOISE

CROSS REFERENCES TO RELATED APPLICATIONS

This application is a continuation of PCT international application Ser. No. PCT/JP2013/079009 filed on Oct. 25, 2013 which designates the United States, incorporated herein by reference, and which claims the benefit of priority from Japanese Patent Applications No. 2013-010540, filed on Jan. 23, 2013, incorporated herein by reference.

BACKGROUND OF THE INVENTION

1. Field of the Invention

The present invention relates to an imaging device, an endoscope system including the imaging device, and a method of eliminating noise with the imaging device.

2. Description of the Related Art

Conventionally, for imaging devices having complementary metal-oxide semiconductor (CMOS) image sensors, in order to eliminate fixed pattern noise due to variation of transistors among pixel columns and reset noise of charge-voltage converters within unit pixels, provision of a noise eliminating unit for each pixel column has been known (see, for example, Japanese Patent Application Laid-open No. 2000-59691).

FIG. 15 is a circuit diagram illustrating a configuration of a conventional imaging device. In this example, a case, in which an imaging device 500 has a CMOS image sensor, will be described.

The imaging device 500, for example, is arranged at a distal end portion of an endoscope and includes a light receiving unit and a reading unit. The light receiving unit is configured of: a plurality of unit pixels 530, which are arranged in a two dimensional matrix form over a plurality of rows and a plurality of columns; and a vertical transfer line 539, which transfers a signal output from each of the unit pixels 530. The reading unit is configured of: a vertical scanning unit (row selection circuit) 541; a noise eliminating unit 543, which is provided for each pixel column; and a horizontal scanning unit (column selection circuit) 558.

Each of the unit pixels 530 includes: a photodiode, which accumulates a signal charge according to an amount of incident light; a charge converter, which performs voltage conversion on a signal charge transferred from the photodiode; a transfer transistor, which transfers the signal charge from the photodiode to the charge converter; a reset transistor, which resets the signal charge transferred to the charge converter; a row selection transistor; and an output transistor, which outputs, as an imaging signal, a change in voltage level of the signal charge subjected to the voltage conversion, to a corresponding vertical transfer line 539 in a source follower, when the row selection transistor is in an ON state.

The reading unit turns a row selection transistor of an arbitrary row in the ON state by the vertical scanning unit (row selection circuit) 541 and reads out the imaging signal to the vertical transfer line 539. The read out imaging signal is input to the noise eliminating unit 543 and a noise component thereof is removed. Thereafter, output as image information to outside is performed by the horizontal scanning unit 558.

FIG. 16 is a circuit diagram illustrating a configuration of the noise eliminating unit of the imaging device illustrated in FIG. 15. The noise eliminating unit 543 includes: a transistor 544 for sampling and holding, with one end side thereof connected to the vertical transfer line 539; a coupling condenser (AC coupling capacitor) CC with one end side thereof connected to another end side of the transistor 544; a charge accumulation condenser (sampling capacitor) CS, which is connected between another end side of the AC coupling capacitor CC and ground; and a potential clamp transistor 545, which is connected to a connection node SN between the AC coupling capacitor CC and the sampling capacitor CS. The connection node SN is connected to the horizontal scanning unit 558.

The noise eliminating unit 543 first turns the transistor 544 for sampling and holding to an ON state upon pixel resetting, transmits, by the AC coupling capacitor CC, a noise signal transferred by the vertical transfer line 539, turns the potential clamp transistor 545 to an ON state for a predetermined time period, and samples a noise signal level in the sampling capacitor CS. Thereafter, when the imaging signal is read out, the imaging signal including the noise signal (light-noise sum signal) is transmitted by the AC coupling capacitor CC again. Since a voltage change of the imaging signal after the pixel resetting is transmitted, as a result, the imaging signal from which the noise signal has been subtracted is able to be taken out from the light-noise sum signal.

SUMMARY OF THE INVENTION

An imaging device according to one aspect of the present invention includes: a photoelectric conversion element that performs photoelectric conversion according to an amount of light received and accumulates a charge; a first transfer unit that transfers the accumulated charge; a charge converter that converts the transferred charge to a voltage or current signal; a charge converter resetting unit that resets the charge converter to a first voltage; a signal output unit that outputs the converted signal; a first transfer line connected to the signal output unit; a transfer capacitor connected to the first transfer line; a second transfer unit that is connected to the first transfer line via the transfer capacitor and to which a signal is output from the first transfer line due to coupling by a capacity of the transfer capacitor; a transfer capacitor resetting unit that resets the transfer capacitor to a second voltage; a second transfer line to which a signal from the second transfer unit is output; a drive unit that causes a signal to be output from the first transfer line via the second transfer unit by a noise signal reading operation and a light-noise sum signal reading operation, the noise signal reading operation resetting the transfer capacitor by the transfer capacitor resetting unit when the signal of the charge converter is output to the first transfer line via the signal output unit after the first transfer unit is turned into an OFF state and the charge converter is reset by the charge converter resetting unit, and the light-noise sum signal reading operation outputting the signal of the charge converter to the first transfer line via the signal output unit after the transfer capacitor resetting unit is turned into an OFF state, the first transfer unit is turned into an ON state, and the charge accumulated by the photoelectric conversion element is transferred; a reference voltage generating unit that generates a reference voltage having a fluctuation component in phase with the second voltage; and an output selector that is connected to the second transfer line and the reference voltage generating unit, and selects and outputs a signal input from the second transfer line and the reference voltage input from the reference voltage generating unit.

An imaging device according to another aspect of the present invention includes: a photoelectric conversion element that performs photoelectric conversion according to an amount of light received and accumulates a charge; a first transfer unit that transfers the accumulated charge; a charge converter that converts the transferred charge to a voltage or current signal; a charge converter resetting unit that resets the charge converter to a first voltage; a signal output unit that outputs the converted signal; a first transfer line connected to the signal output unit; a transfer capacitor connected to the first transfer line; a second transfer unit that is connected to the first transfer line via the transfer capacitor and to which a signal is output from the first transfer line due to coupling by a capacity of the transfer capacitor; a transfer capacitor resetting unit that resets the transfer capacitor to a second voltage; a second transfer line to which a signal from the second transfer unit is output; a reference voltage generating unit that generates a reference voltage based on the first voltage and comprises a reference voltage generating unit resetting unit that resets a voltage of the reference voltage generating unit to the first voltage, a reference voltage generating unit signal output unit that outputs a signal of the reference voltage generating unit resetting unit, and a third transfer unit that outputs, as the reference voltage, a signal from the reference voltage generating unit signal output unit to the second transfer line; and a drive unit that causes a signal to be output from the first transfer line via the second transfer unit by a noise signal reading operation and a light-noise sum signal reading operation, and drives the second transfer unit and the third transfer unit such that the signal output from the first transfer line and the reference voltage are alternately output to the second transfer line, the noise signal reading operation resetting the transfer capacitor by the transfer capacitor resetting unit when the signal of the charge converter is output to the first transfer line via the signal output unit after the first transfer unit is turned into an OFF state and the charge converter is reset by the charge converter resetting unit, and the light-noise sum signal reading operation outputting the signal of the charge converter to the first transfer line via the signal output unit after the transfer capacitor resetting unit is turned into an OFF state, the first transfer unit is turned into an ON state, and the charge accumulated by the photoelectric conversion element is transferred.

A method of eliminating noise according to still another aspect of the present invention is a method of eliminating noise in an imaging device, which includes: a photoelectric conversion element that performs photoelectric conversion according to an amount of light received and accumulates a charge; a first transfer unit that transfers the accumulated charge; a charge converter that converts the transferred charge to a voltage or current signal; a charge converter resetting unit that resets the charge converter to a first voltage; a signal output unit that outputs the converted signal; a first transfer line connected to the signal output unit; a transfer capacitor connected to the first transfer line; a second transfer unit that is connected to the first transfer line via the transfer capacitor and to which a signal is output from the first transfer line due to coupling by a capacity of the transfer capacitor; a transfer capacitor resetting unit that resets the transfer capacitor to a second voltage; and a second transfer line to which a signal from the second transfer unit is output. The method includes: turning the first transfer unit into an OFF state and resetting the charge converter by the charge converter resetting unit; resetting the transfer capacitor by the transfer capacitor resetting unit when the signal of the charge converter is output to the first transfer line via the signal output unit; turning the transfer capacitor resetting unit into an OFF state, turning the first transfer unit into an ON state, and transferring the charge accumulated by the photoelectric conversion element; outputting the signal of the charge converter to the first transfer line via the signal output unit; causing a signal to be output from the first transfer line via the second transfer unit; reference voltage generation of generating a reference voltage having a fluctuation component in phase with the second voltage; and output and selection of selecting and outputting a signal input from the second transfer line and the reference voltage generated in the reference voltage generation.

A method of eliminating noise according to yet another aspect of the present invention is a method of eliminating noise in an imaging device, which includes: a photoelectric conversion element that performs photoelectric conversion according to an amount of light received and accumulates a charge; a first transfer unit that transfers the accumulated charge; a charge converter that converts the transferred charge to a voltage or current signal; a charge converter resetting unit that resets the charge converter to a first voltage; a signal output unit that outputs the converted signal; a first transfer line connected to the signal output unit; a transfer capacitor connected to the first transfer line; a second transfer unit that is connected to the first transfer line via the transfer capacitor and to which a signal is output from the first transfer line due to coupling by a capacity of the transfer capacitor; a transfer capacitor resetting unit that resets the transfer capacitor to a second voltage; a second transfer line to which a signal from the second transfer unit is output; and a reference voltage generating unit that generates a reference voltage based on the first voltage and comprises a reference voltage generating unit resetting unit that resets a voltage of the reference voltage generating unit to the first voltage, a reference voltage generating unit signal output unit that outputs a signal of the reference voltage generating unit resetting unit, and a third transfer unit that outputs, as the reference voltage, a signal from the reference voltage generating unit signal output unit to the second transfer line. The method includes: turning the first transfer unit into an OFF state and resetting the charge converter by the charge converter resetting unit; resetting the transfer capacitor by the transfer capacitor resetting unit when the signal of the charge converter is output to the first transfer line via the signal output unit; turning the transfer capacitor resetting unit into an OFF state, turning the first transfer unit into an ON state, and transferring the charge accumulated by the photoelectric conversion element; outputting the signal of the charge converter to the first transfer line via the signal output unit; and driving the second transfer unit and the third transfer unit such that a signal output from the first transfer line and the reference voltage are alternately output to the second transfer line.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

In the following description, as modes for carrying out the present invention (hereinafter, referred to as "embodiments"), endoscope systems including imaging devices will be described. Further, the present invention is not limited by these embodiments. Furthermore, in describing the drawings, identical reference signs are appended to the same portions. Moreover, the drawings are schematic, and it is necessary to note that the relation between the thickness and width of each component and the ratios among the respective components are different from the actual. In addition, a portion is included, which has different sizes and ratios among the drawings.

First Embodiment

Figure 1:
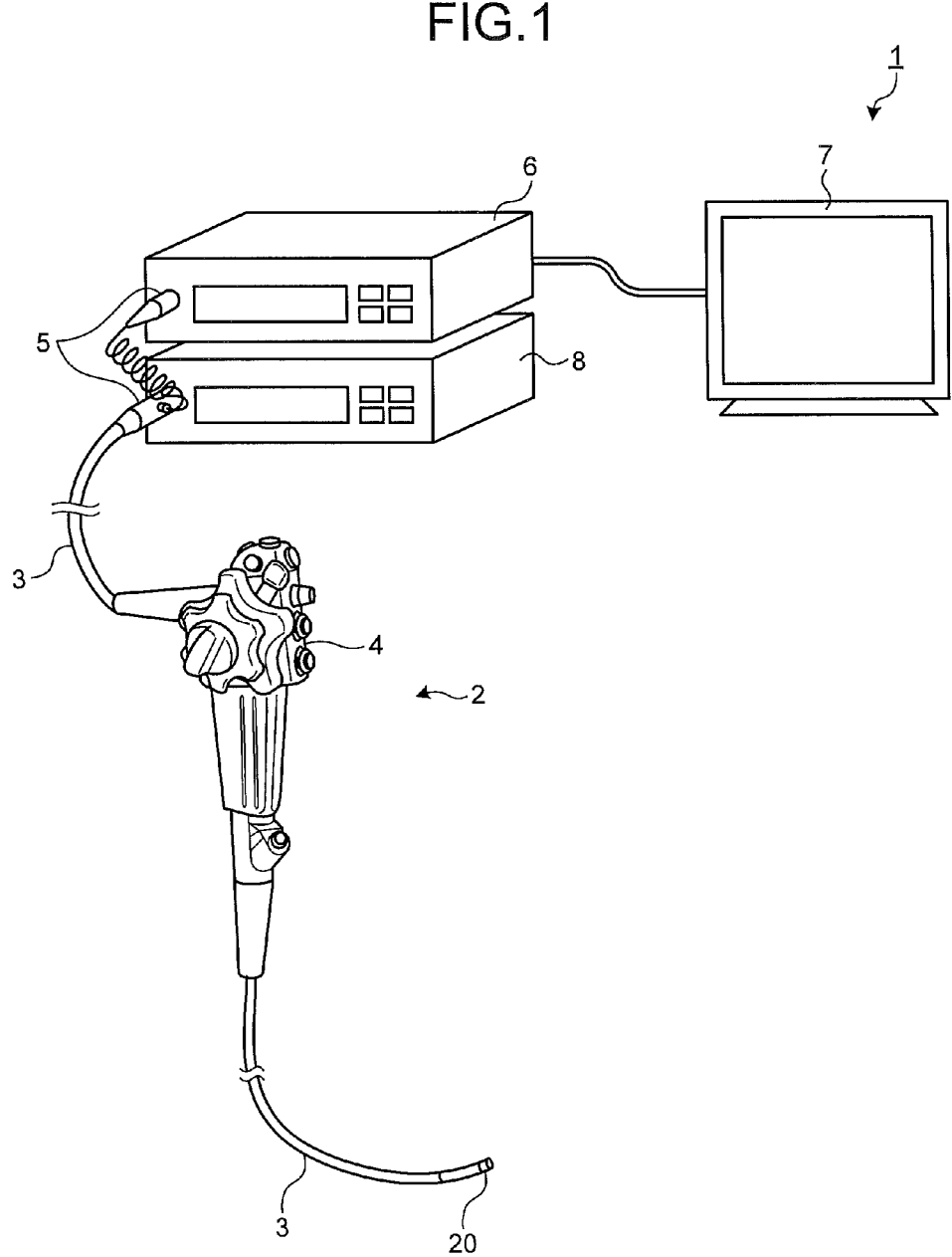
FIG. 1 is a diagram schematically illustrating an overall configuration of an endoscope system according to a first embodiment of the present invention.

FIG. 1 is a diagram schematically illustrating an overall configuration of an endoscope system according to a first embodiment of the present invention. An endoscope system 1 illustrated in the figure includes an endoscope 2, a transmission cable 3, a connector unit 5, a processor (control device) 6, a display device 7, and a light source device. The endoscope 2 captures an in-vivo image of a subject and outputs an imaging signal, by insertion of a distal end portion thereof into a body cavity of the subject. The transmission cable 3 connects the endoscope 2 with the connector unit 5. The connector unit 5 is connected to the endoscope 2, the processor 6, and a light source device 8, performs predetermined signal processing on the imaging signal output by the endoscope 2 connected thereto, performs analog-digital conversion (A/D conversion) on the imaging signal, and outputs the converted imaging signal as an image signal. The processor 6 performs predetermined image processing on the image signal output from the connector unit 5 and controls the whole endoscope system 1. The display device 7 displays the image signal processed by the processor 6. The light source device 8 is, for example, configured by using a white LED. Pulsed white light lighted by the light source device 8 reaches, via the connector unit 5 and the transmission cable 3, a distal end portion of an insertion portion of the endoscope 2 and becomes illumination light to be irradiated towards the subject from that distal end portion.

The endoscope 2 is provided with, at a distal end side of the insertion portion to be inserted into the body cavity of the subject, an imaging unit (imaging device) 20 that captures the in-vivo images, and an operating unit 4 that receives various operations with respect to the endoscope 2 is connected to a proximal end side of the insertion portion. The imaging unit 20 is connected to the connector unit 5 by the transmission cable 3, via the operating unit 4. The imaging signal of an image captured by the imaging unit 20, for example, passes through the transmission cable 3 having a length of a few meters, and is output to the connector unit 5.

Figure 2:
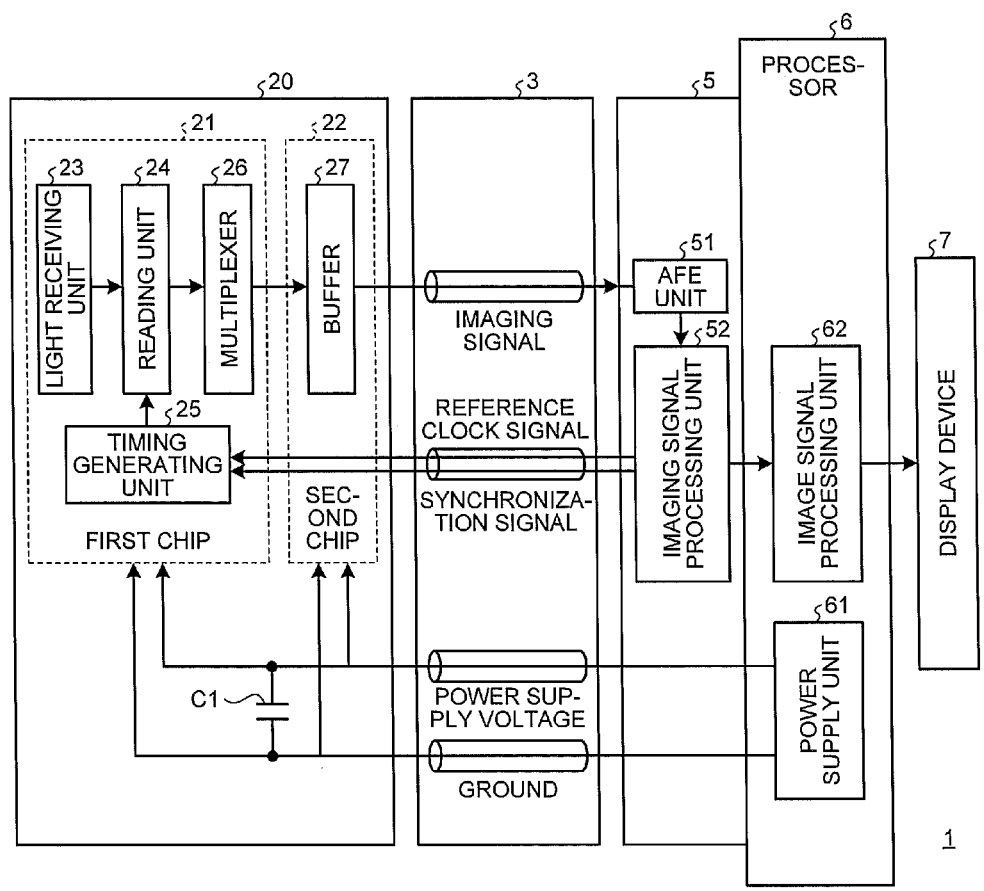
FIG. 2 is a block diagram illustrating functions of main parts of the endoscope system according to the first embodiment of the present invention.

FIG. 2 is a block diagram illustrating functions of main parts of the endoscope system according to the first embodiment of the present invention. With reference to FIG. 2, details of each component of the endoscope system 1 and a route of an electric signal in the endoscope system 1 will be described.

The imaging unit 20 includes a first chip 21 having a light receiving unit 23, and a second chip 22 having a buffer 27. The first chip 21 and second chip 22 are stuck opposed to each other, and the chips are connected by pads arranged at peripheral edge portions of the chips, vias penetrating through the chips, or the like. The first chip 21 and second chip 22 are not limited to those arranged such that principal planes thereof become parallel to each other, and according to a structure of their surroundings, may be arrange side by side or arranged such that with respect to one of the principal surfaces, the other one of the principal surfaces becomes vertical.

The first chip 21 of the imaging unit 20 includes: the light receiving unit 23 in which multiple unit pixels are arranged in a two dimensional matrix form in both row and column directions; a reading unit 24 that reads out an imaging signal photoelectrically converted in the light receiving unit 23; a timing generating unit 25 that generates a timing signal based on a reference clock signal and a synchronization signal sent out from the connector unit 5 and supplies the timing signal to the reading unit 24; and a multiplexer 26 that outputs the imaging signal to the second chip 22. A more detailed configuration of the first chip 21 will be described in detail later with reference to FIG. 3.

The second chip 22 of the imaging unit 20 includes a buffer 27 that functions as a transmitting unit, which transmits, via the transmission cable 3 and the connector unit 5, to the processor 6, only an alternating current component of the imaging signal output from the first chip 21. Combinations of circuits mounted on the first chip 21 and second chip 22 may be changed as appropriate according to design conditions.

Further, the imaging unit 20 receives, via the transmission cable 3, power supply voltage (VDD) generated in a power supply unit 61 in the processor 6, together with ground (GND). Between the power supply voltage (VDD) and the ground (GND) supplied to the imaging unit 20, a condenser C1 for power supply stabilization is provided.

The connector unit 5 includes an analog front end (AFE) unit 51 and an imaging signal processing unit 52. The connector unit 5 functions as a relay processing unit that electrically connects the endoscope 2 (imaging unit 20) with the processor 6 and relays an electric signal. The connector unit 5 and the imaging unit 20 are connected to each other by the transmission cable 3 and the connector unit 5 and the processor 6 are, for example, connected by a coil cable. Further, the connector unit 5 is connected also to the light source device 8.

The AFE unit 51 receives the imaging signal transmitted from the imaging unit 20, and after performing impedance matching by a passive element, such as a resistance, takes out an alternating current component by a condenser and determines an operating point by a partial resistance. Thereafter, the AFE unit 51 performs analog-digital (A/D) conversion on an analog imaging signal and transmits the converted signal as a digital imaging signal to the imaging signal processing unit 52.

The imaging signal processing unit 52, for example, is configured of a field programmable gate array (FPGA), generates a reference clock signal to be a reference of operation of each component of the endoscope 2 (for example, a clock of 27 MHz) and a synchronization signal representing a start position of each frame, supplies the generated signals to the timing generating unit 25, and performs predetermined signal processing, such as noise elimination, on the digital imaging signal input from the AFE unit 51.

The processor 6 is configured by including the power supply unit 61 and an image signal processing unit 62, and is a control device that controls the whole endoscope system 1. The power supply unit 61 generates the power supply voltage (VDD) and supplies to the imaging unit 20, via the connector unit 5 and the transmission cable 3, this generated power supply voltage, together with the ground (GND). The image signal processing unit 62 performs predetermined image processing on the digital imaging signal subjected to the signal processing, such as noise elimination, by the imaging signal processing unit 52, and outputs the processed signal as an image signal to the display device 7.

The display device 7, displays an image captured by the imaging unit 20, based on the image signal. The image processing in the image signal processing unit 62 is, for example, a synchronization process, a white balance (WB) adjustment process, a gain adjustment process, a gamma correction process, a digital-analog (D/A) conversion process, a format conversion process, or the like.

Figure 3:
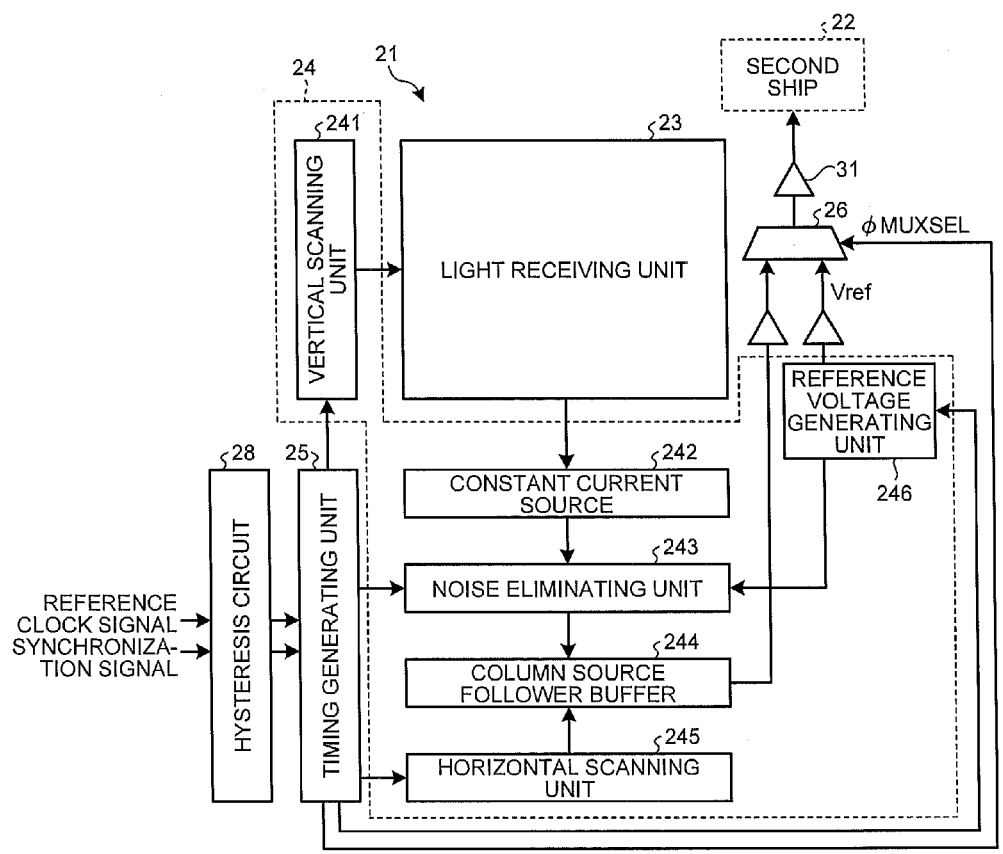
FIG. 3 is a block diagram illustrating details of a first chip illustrated in FIG. 2.
Figure 4:
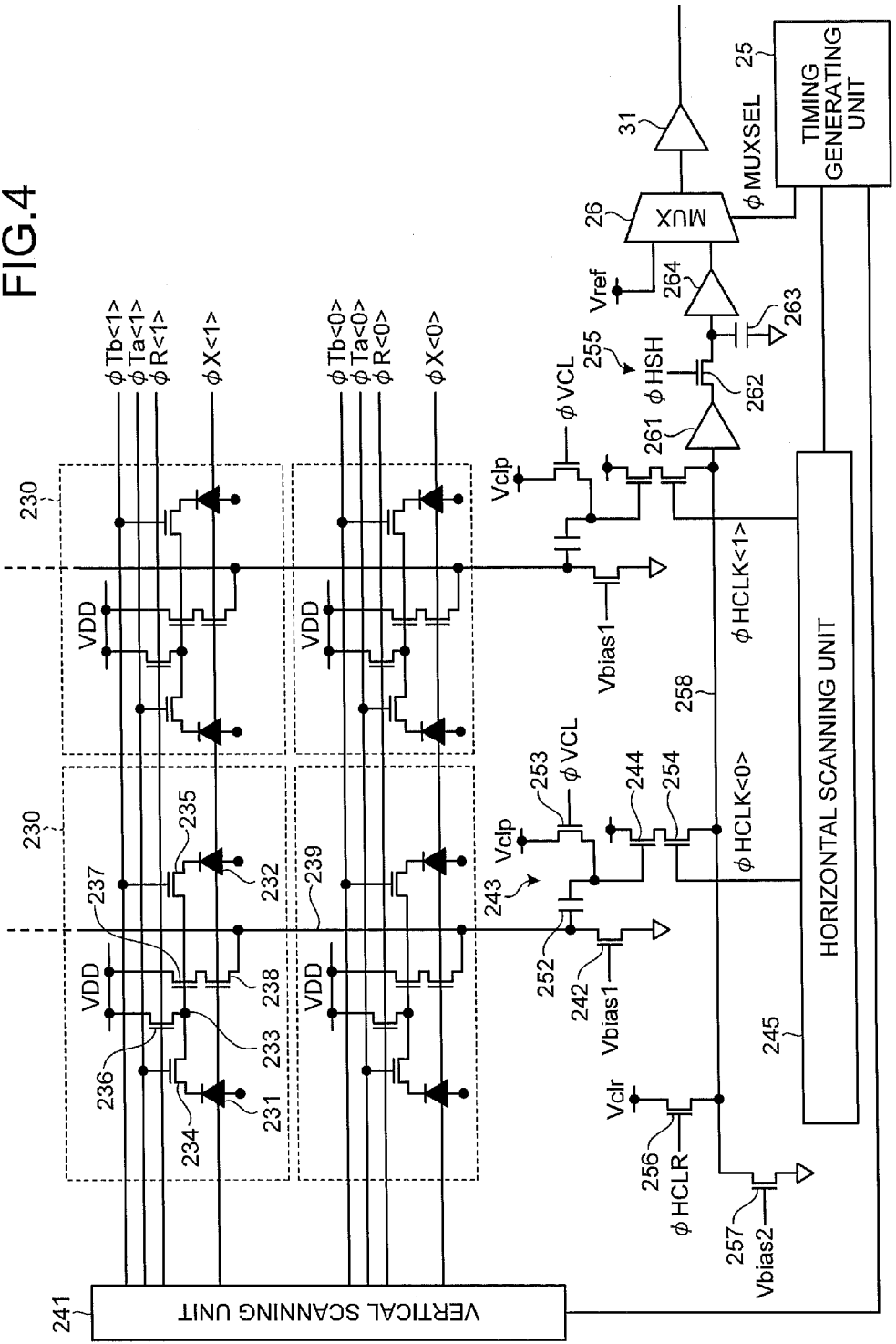
FIG. 4 is a circuit diagram illustrating a configuration of the first chip of the endoscope system according to the first embodiment.

FIG. 3 is a block diagram illustrating a detailed configuration of the first chip illustrated in FIG. 2. FIG. 4 is a circuit diagram illustrating a configuration of the first chip of the endoscope system according to the first embodiment. On the first chip 21, for example, the light receiving unit 23, the reading unit (drive unit) 24, the timing generating unit 25, and the multiplexer 26 are mounted. Details of the light receiving unit 23 will be described later with reference to FIG. 4. At a previous stage of the timing generating unit 25, that is, between an input of the timing generating unit 25 and the processor 6, a hysteresis circuit 28 is provided. The hysteresis circuit 28 performs waveform shaping of the reference clock signal and synchronization signal transmitted over a long distance by the transmission cable 3. The reference clock signal and synchronization signal subjected to the waveform shaping by the hysteresis circuit 28 are input to the timing generating unit 25.

Based on the reference clock signal and synchronization signal shaped by the hysteresis circuit 28, the timing generating unit 25 generates various drive signals (φTa, φTb, φR, φX, φVCL, φHCLR, φHCLK, φMUXSEL, and φVSH) and supplies them to a vertical scanning unit 241, a noise eliminating unit 243, a horizontal scanning unit 245, the multiplexer 26, and a reference voltage generating unit 246.

The reading unit 24 includes the vertical scanning unit (row selection circuit) 241, a constant current source 242, the noise eliminating unit 243, a column source follower buffer (transistor) 244, the horizontal scanning unit (column selection circuit) 245, and the reference voltage generating unit 246.

Based on the drive signals (φT, φR, and X) supplied from the timing generating unit 25, the vertical scanning unit 241 applies row selection pulses φTa<N>, φTb<N>, φR<N>, and φX<N>, to a selected row <N> (N=0, 1, 2, . . . , n−1, n) of the light receiving unit 23, drives each unit pixel 230 of the light receiving unit 23 by the constant current source 242, transfers to a vertical transfer line 239 and outputs to the noise eliminating unit 243, an imaging signal and a noise signal upon pixel resetting.

The noise eliminating unit 243 eliminates output variation for each unit pixel 230 and the noise signal upon pixel resetting, and outputs an imaging signal photoelectrically converted by each unit pixel 230 to the column source follower buffer 244. Details of the noise eliminating unit 243 will be described later with reference to FIG. 4.

Based on the drive signal (φHCLK) supplied from the timing generating unit 25, the horizontal scanning unit 245 applies a column selection pulse φHCLK<M> to a selected column <M> (M=0, 1, 2, . . . , m−1, m) of the light receiving unit 23 and transfers to a horizontal transfer line 258 and outputs to the multiplexer 26, via the column source follower buffer 244, an imaging signal photoelectrically converted by each unit pixel 230.

The multiplexer 26 is driven by the drive signal (φMUXSEL) supplied from the timing generating unit 25, and alternately outputs to the second chip 22, via an output unit (amplifier) 31, the imaging signal input through the horizontal transfer line 258 and a reference voltage Vref (constant voltage signal) generated by the reference voltage generating unit 246. This output reference voltage Vref is used in the imaging signal processing unit 52 or the like of the connector unit 5 for elimination of in-phase noise superimposed in the transmission cable 3 during transmission of the imaging signal. As necessary, an amplifier for gain adjustment may be provided at an input side of the multiplexer 26.

In the light receiving unit 23 of the first chip 21, multiple unit pixels 230 are arranged in a two dimensional matrix form. Each of the unit pixels 230 includes photoelectric conversion elements (photodiodes) 231 and 232, a charge converter 233, transfer transistors (first transfer unit) 234 and 235, a charge converter resetting unit (transistor) 236, a pixel source follower transistor 237, and a pixel output switch (signal output unit) 238. In this specification, one or more photoelectric conversion elements and a transfer transistor for transferring a signal charge from each photoelectric conversion element to the charge converter 233 are called a unit cell. That is, in a unit cell, a set of: one or a plurality of photo electric conversion elements; and a transfer transistor, is included, and in each unit pixel 230, one unit cell is included.

The photoelectric conversion elements 231 and 232 photoelectrically convert and accumulate incident light to a signal charge quantity corresponding to a light quantity thereof. Cathode sides of the photoelectric conversion elements 231 and 232 are respectively connected to one end sides of the transfer transistors 234 and 235 and anode sides thereof are connected to the ground GND. The charge converter 233 is formed of a floating diffusion capacitor (FD) and converts the charge accumulated in the photoelectric conversion elements 231 and 232 into voltages.

The transfer transistors 234 and 235 transfer the charge from the photoelectric conversion elements 231 and 232 to the charge converter 233 respectively. To gates of the transfer transistors 234 and 235, signal lines, to which drive pulses (row selection pulses) φTa and φTb are supplied, are respectively connected, and other end sides thereof are connected to the charge converter 233. When the drive pulses φTa and φTb are supplied from the vertical scanning unit 241 via the signal line, the transfer transistors 234 and 235 are turned into an ON state and signal charge is transferred from the photoelectric conversion elements 231 and 232 to the charge converter 233.

The charge converter resetting unit (transistor) 236 resets the charge converter 233 to a predetermined potential. One end side of the charge converter resetting unit 236 is connected to the power supply voltage VDD, another end side thereof is connected to the charge converter 233, and to a gate thereof, a signal line, to which the drive pulse φR is supplied, is connected. When φR is supplied from the vertical scanning unit 241 via the signal line, the charge converter resetting unit 236 is turned into an ON state, the signal charge that has accumulated in the charge converter 233 is released, and the charge converter 233 is reset to a predetermined potential.

One end side of the pixel source follower transistor 237 is connected to the power supply voltage VDD, and another end side thereof is connected to one end side of the pixel output switch 238. To a gate thereof, a signal subjected to voltage conversion by the charge converter 233 (imaging signal or signal upon resetting) is input. The pixel output switch 238 outputs the signal subjected to the voltage conversion by the charge converter 233 to the vertical transfer line 239. Another end side of the pixel output switch 238 is connected to the vertical transfer line 239 and to a gate thereof, a signal line, to which the drive pulse φX is supplied, is connected. When the drive pulse φX is supplied from the vertical scanning unit 241 via the signal line to the gate of the pixel output switch 238, the pixel output switch 238 is turned into an ON state, and the imaging signal or the signal upon resetting is transferred to the vertical transfer line 239.

One end side of the constant current source 242 is connected to the vertical transfer line 239, another end side thereof is connected to the ground GND, and to a gate thereof, a bias voltage Vbias1 is applied. The unit pixels 230 are driven by the constant current source 242 and output of the unit pixels is read out to the vertical transfer line 239. The signals read out to the vertical transfer line 239 are input to the noise eliminating unit 243.

The noise eliminating unit 243 includes a transfer capacitor (AC coupling condenser) 252 and a clamp switch (transistor) 253. One end side of the transfer capacitor 252 is connected to the vertical transfer line 239, and another end side thereof is connected to the column source follower transistor 244. One end side of the clamp switch 253 is connected to a signal line, to which a clamp voltage Vclp is supplied from the reference voltage generating unit 246. Another end side of the clamp switch 253 is connected between the transfer capacitor 252 and the column source follower transistor 244, and to a gate thereof, the drive signal φVCL is input from the timing generating unit 25. The imaging signal input from the noise eliminating unit 243 is a light-noise sum signal including a noise component.

When the drive signal φVCL is input from the timing generating unit 25 to the gate of the clamp switch 253, the clamp switch 253 is turned into an ON state, and the transfer capacitor 252 is reset by the clamp voltage Vclp supplied from the reference voltage generating unit 246. An imaging signal subjected to noise elimination by the noise eliminating unit 243 is input to a gate of the column source follower transistor 244.

The noise eliminating unit 243 does not require a condenser for sampling (sampling capacitor) and thus a capacity of the transfer capacitor (AC coupling condenser) 252 just needs to be a capacity sufficient with respect to an input capacity of the column source follower transistor 244. In addition, because of the lack of the sampling capacitor, an area occupied by the noise eliminating unit 243 on the first chip 21 is able to be decreased.

One end side of the column source follower transistor 244 is connected to the power supply voltage VDD, another end side thereof is connected to one end side of a column selection switch (second transfer unit) 254, and to the gate thereof, the imaging signal subjected to the noise elimination in the noise eliminating unit 243 is input. The one end side of the column selection switch 254 is connected to the another end side of the column source follower transistor 244, and another end side of the column selection switch 254 is connected to the horizontal transfer line (second transfer line) 258. To the gate of the column selection switch 254, a signal line for supplying the drive signal φHCLK<M> from the horizontal scanning unit 245 is connected. When the drive signal φHCLK<M> is supplied from the horizontal scanning unit 245 to the gate of the column selection switch 254 of column <M>, the column selection switch 254 is turned into an ON state, and a signal of the vertical transfer line 239 of column <M> (the imaging signal subjected to the noise elimination in the noise eliminating unit 243) is transferred to the horizontal transfer line 258.

One end side of a constant current source 257 is connected to the horizontal transfer line 258, another end side thereof is connected to the ground GND, and to a gate thereof, a bias voltage Vbias2 is applied. The constant current source 257 reads out an imaging signal from the vertical transfer line 239 to the horizontal transfer line 258. The signal read out to the horizontal transfer line 258 is input to sampling and holding unit 255.

One end side of a horizontal resetting transistor 256 is connected to a horizontal resetting voltage Vclr, and another end side thereof is connected to the horizontal transfer line 258. To a gate of the horizontal resetting transistor 256, the drive signal φHCLR is input from the timing generating unit 25. When the drive signal φHCLR is input to the gate of the horizontal resetting transistor 256 from the timing generating unit 25, the horizontal resetting transistor 256 is turned into an ON state and the horizontal transfer line 258 is reset.

The sampling and holding unit 255 includes a buffer 261, a sampling and holding switch (transistor) 262, a sampling capacitor (condenser) 2634, and an operational amplifier 264. To an input of the buffer 261, the horizontal transfer line 258 is connected, and via this horizontal transfer line 258, an imaging signal and a noise signal upon the horizontal resetting are input to the buffer 261. An output of the buffer 261 is connected to one end side of the sampling and holding switch 262. Another end side of the sampling and holding switch 262 is connected to an input of the operational amplifier 264. One end side of a sampling capacitor 263 is connected to the another end side of the sampling and holding switch 262 and the input of the operational amplifier 264, and another end side of the sampling capacitor 263 is connected to the ground GND. An output of the operational amplifier 264 is connected to an inversion input terminal of the operational amplifier 264 and connected to an input of the multiplexer 26. The sampling and holding unit 255 holds, in the sampling capacitor 263, a voltage immediately before the sampling and holding switch 262 is turned into an OFF state and while the sampling and holding switch 262 is in the OFF state, outputs the voltage held in the sampling capacitor 263.

In the first embodiment, by alternately performing reading of the imaging signal after the noise elimination from the vertical transfer line 239 and resetting of the horizontal transfer line 258 by the horizontal resetting transistor 256, crosstalk of the imaging signal in the column direction is able to be suppressed. Further, by turning the sampling and holding switch 262 of the sampling and holding unit 255 into the ON state when the imaging signal after the noise elimination is transferred and into the OFF state when the noise signal upon the resetting is transferred, only the imaging signal after the noise elimination is able to be output to the operational amplifier 264. By the first chip 21 including the sampling and holding unit 255, a band of am amplifying circuit at a later stage is able to be halved and a range thereof is able to be suppressed.

The multiplexer 26 alternately outputs, to the output unit 31, the noise-eliminated imaging signal output from the sampling and holding unit 255 and the reference voltage Vref generated by the reference voltage generating unit 246. The output unit 31 performs signal amplification as necessary on the noise-eliminated imaging signal and the reference voltage Vref and alternately outputs them to the second chip 22.

In the second chip 22, only the alternating current components of the noise-eliminated imaging signal and the reference voltage Vref are transmitted to the connector unit 5 via the transmission cable 3.

Figure 5:
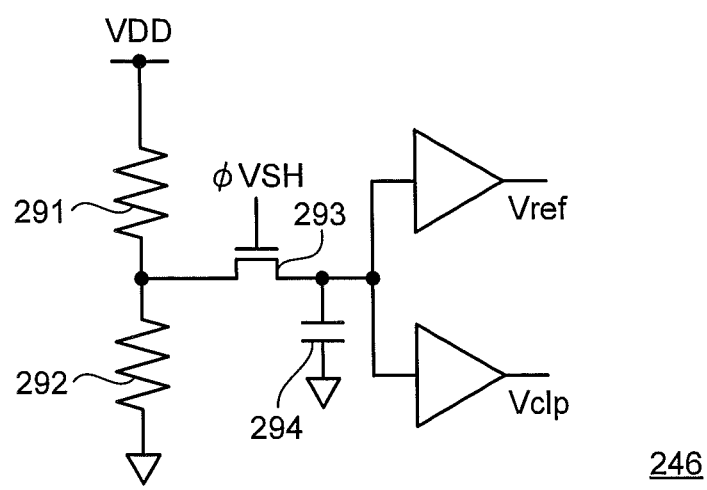
FIG. 5 is a circuit diagram illustrating a configuration of a reference voltage generating unit of the endoscope system according to the first embodiment.

FIG. 5 is a circuit diagram illustrating a configuration of the reference voltage generating unit of the light receiving unit of the endoscope system according to the first embodiment. The reference voltage generating unit (constant voltage signal generating unit) 246 includes a resistance voltage dividing circuit formed of two resistances 291 and 292, a switch (transistor) 293 driven by the drive signal φVSH, and a sampling capacitor (condenser) 294 for releasing from fluctuation independently of a power supply. The reference voltage generating unit 246 generates the reference voltage Vref (constant voltage signal) and the clamp voltage Vclp of the noise eliminating unit 243 from the power supply voltage VDD, that is the same as that of the light receiving unit 23, at the timing in which the drive signal φVSH drives by driving of the switch 293.

Since the reference voltage Vref and the clamp voltage Vclp are generated at the same timing from the same power supply, the reference voltage Vref reflects influence of power supply fluctuation on the imaging signal output from the noise eliminating unit 243. Further, the reference voltage Vref reflects transmission noise information in the transmission cable 3 during transmission. Therefore, by transmitting alternately the noise-eliminated imaging signal and the reference voltage Vref to the connector unit 5, in the connector unit 5, a noise eliminating process, such as correlated double sampling, is able to be performed and an imaging signal, from which the noise during the transmission has been eliminated, is able to be acquired.

Figure 6:
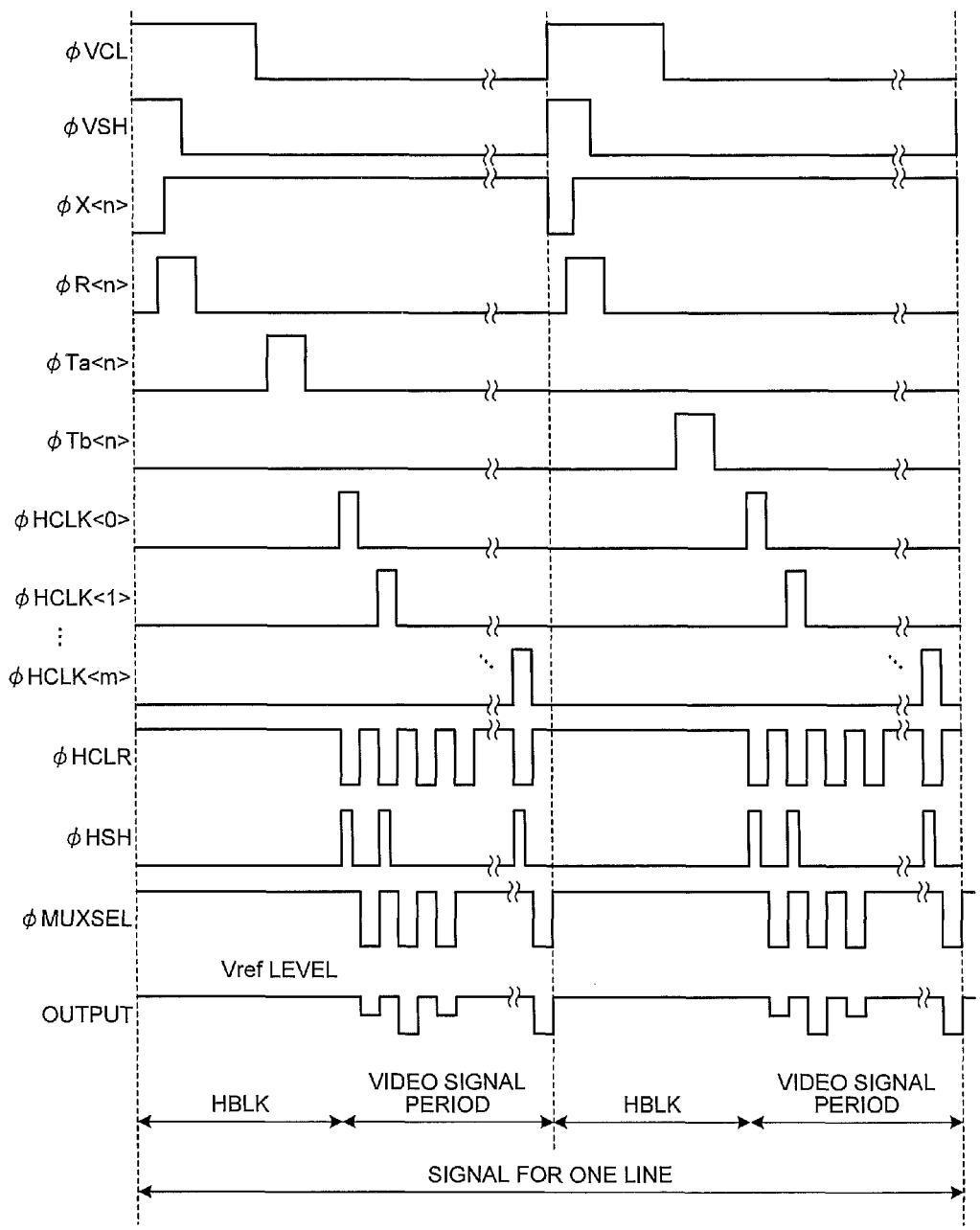
FIG. 6 is a timing chart illustrating driving signals of an imaging device according to the first embodiment.

FIG. 6 is a timing chart illustrating driving signals of the imaging device according to the first embodiment. In this example, from reading of a signal from a unit pixel 230 of row<n> of the light receiving unit 23 and outputting it from the output unit 31 will be described.

First, the clamp switch 253 is turned ON (φVCL is High), a pixel output switch 238 is turned ON (φX<n> is High), the charge converter resetting unit 236 is turned ON in a pulsed manner (drive pulse φR<n> is High), the transfer transistors 234 and 235 are turned OFF (the drive pulses φTa<n> and φTb<n> are Low), to thereby output a noise signal including variation particular to the unit pixel 230 to be read out, noise upon pixel resetting, and the like, from the unit pixel 230 to the vertical transfer line 239. When this is done, by keeping the clamp switch 253 in the ON state (φVCL is High), the gate of the column source follower transistor 244 is set to a voltage of the clamp voltage Vclp. The clamp voltage Vclp is determined at a falling timing of φVSH and the reference voltage Vref is also determined at this timing.

Next, by turning the transfer transistor 234 ON in a pulsed manner (the drive pulse φTa<n> is High) while the clamp switch 253 is in the OFF state (φVCL is Low), a signal, which is obtained by converting the charge photoelectrically converted in the photoelectric conversion element 231 by the charge converter 233, is read out to the vertical transfer line 239. In this state, since the pixel output switch 238 is still ON (φX<n> is High), an imaging signal subjected to the voltage conversion by the charge converter 233 (light-noise sum signal) is transferred to the vertical transfer line 239. By this operation, via the transfer capacitor 252, an imaging signal (optical signal) from which a noise signal has been subtracted, is output to the gate of the column source follower transistor 244. Herein, the signal output to the gate of the column source follower transistor 244 is a signal sampled with reference to the clamp voltage Vclp.

After sampling the imaging signal with reference to the clamp voltage Vclp, the horizontal resetting transistor 256 is turned OFF (φHCLR is Low), resetting of the horizontal transfer line 258 is released, and the column selection switch 254 of row <0> is turned ON (the drive pulse φHCLK<O> is High), to thereby transfer the imaging signal to the horizontal transfer line 258. When that is done, by turning the sampling and holding switch 262 ON in a pulsed form (the drive pulse φHSH is High), the imaging signal is sampled by the sampling capacitor 263. Thereafter, by applying the drive pulse φMUXSEL of a Low level on the multiplexer 26, the imaging signal sampled by the sampling capacitor 263 is output to the output unit 31. When that is done, in synchronization with the drive pulse of the multiplexer 26, the horizontal resetting transistor 256 is turned ON (the drive pulse φHCLR is High), and the horizontal transfer line 258 is reset again.

Further, thereafter, by applying the drive pulse φMUXSEL of a High level to the multiplexer 26, outputting the reference voltage Vref (constant voltage signal) generated by the reference voltage generating unit 246 to the output unit 31, turning the horizontal resetting transistor 256 OFF (φHCLR is Low), releasing resetting of the horizontal transfer line 258 that has been reset, and turning the column selection switch 254 of the next column ON (φHCLK<1> is High), the imaging signal is transferred to the horizontal transfer line 258. When that is done, by turning the sampling and holding switch 262 ON in a pulsed form (the drive pulse φHSH is High), the imaging signal is sampled by the sampling capacitor 263. Then, the horizontal resetting transistor 256 is turned ON (φHCLR is High), the horizontal transfer line 258 is reset again, the drive pulse φMUXSEL of a Low level is applied to the multiplexer 26 in synchronization with the pulse of the horizontal resetting transistor 256, and the sampled imaging signal is output to the output unit 31.

Such an operation is repeated as many times as the number of columns of the light receiving unit 23 (or the number of columns required to be read out), to thereby output alternately the imaging signal and the reference voltage Vref from the output unit 31. Further, for the photoelectric conversion element 232, by performing the same operation, imaging signals for one line are output. Further, by repeating the reading operations for one line as many times as the number of unit pixel rows (or the number of rows required to be read out), image signals for one frame are output.

As described above, according to the first embodiment of the present invention, since the noise eliminating unit 243 does not require a condenser for sampling (a sampling capacitor), a capacity of the transfer capacitor (AC coupling condenser) 252 is able to be suppressed low. Further, since there is no sampling capacitor, an area occupied by the noise eliminating unit 243 is able to be reduced.

Moreover, according to the first embodiment of the present invention, the imaging signal and the reference voltage Vref are able to be output alternately for each pixel. Thereby, for example, in a correlated double sampling circuit provided in the connector unit 5, in-phase noise superimposed during transmission of a signal is able to be removed effectively.

In the above described first embodiment, although the unit cell is configured of the pair of two photoelectric conversion elements 231 and 232 adjacent to each other in the column direction, a unit cell may be configured of a pair of two photoelectric conversion elements adjacent to each other in the row direction, or a unit cell may be configured of a set of four photoelectric conversion elements adjacent to one another in the row direction and column direction. Further, without sharing pixels, a unit cell may be configured of a single photoelectric conversion element.

The sampling and holding unit 255 may be omitted. Even if the sampling and holding unit 255 is omitted, by the multiplexer 26 at the later stage, only the imaging signals are selected, and the imaging signal and the reference voltage Vref are alternately output to the output unit 31.

Modified Example of First Embodiment

Figure 7:
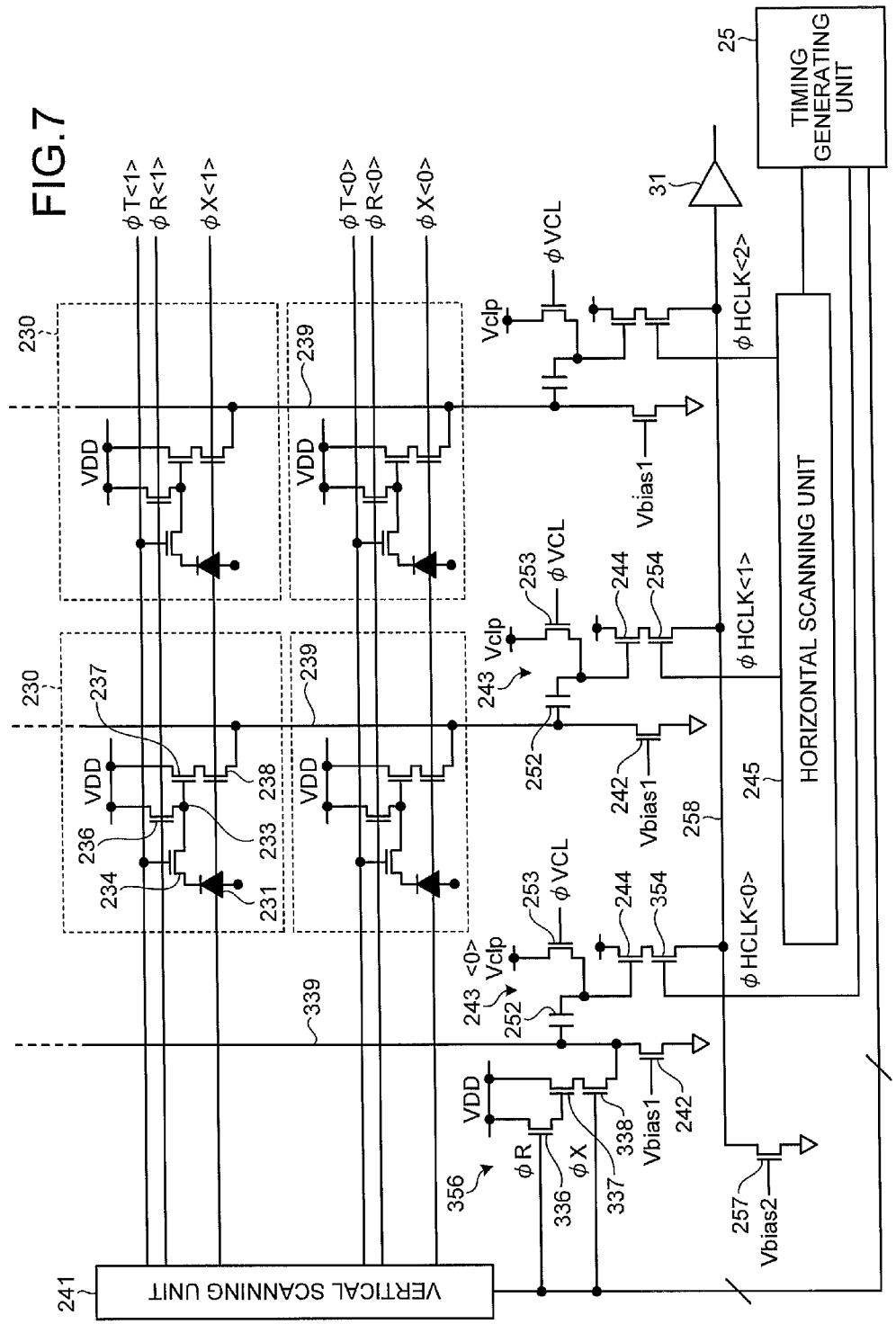
FIG. 7 is a circuit diagram illustrating a configuration of a first chip of an endoscope system according to a modified example of the first embodiment.

FIG. 7 is a circuit diagram illustrating a configuration of a first chip of an endoscope system according to a modified example of the first embodiment. In describing an endoscope system 1 according to this modified example of the first embodiment, to structural elements that are the same as those of the endoscope system 1 according to the first embodiment, the same reference signs will be appended and detailed description thereof will be omitted.

In this modified example of the first embodiment, instead of the horizontal resetting transistor 256 of FIG. 4, a reference voltage generating unit 356 is connected between the vertical scanning unit 241 and the timing generating unit 25, and connected with the horizontal transfer line 258 via the noise eliminating unit 243 of column <0>. Further, in this modified example, one photoelectric conversion element 231 is included in a unit pixel 230 without pixel sharing. The rest of the circuit configuration is similar to that of the first embodiment.

The reference voltage generating unit 356 includes a resetting unit (transistor) 336, a source follower transistor 337, and an output switch (transistor) 338. One end side of the resetting unit 336 is connected to the power supply voltage VDD, another end side thereof is connected to a gate of the source follower transistor 337, and to a gate thereof, a signal line, to which the drive pulse φR is supplied, is connected. When the drive pulse φR is supplied from the timing generating unit 25 via the signal line, the resetting unit 336 is turned into an ON state, and to the gate of the source follower transistor 337, a signal upon resetting is input. One end side of the source follower transistor 337 is connected to the power supply voltage VDD, and another end side thereof is connected to one end side of the output switch 338. Another end side of the output switch 338 is connected to a vertical transfer line 339 and to a gate of the output switch 338, a signal line, to which the drive pulse φX is supplied, is connected. When the drive pulse φX is supplied to the gate of the output switch 338 via the signal line from the timing generating unit 25, the output switch 338 is turned into an ON state, and a signal upon resetting is transferred to the vertical transfer line 339 for the reference voltage generating unit 356. Noise is eliminated by the noise eliminating unit 243 from the signal upon resetting (reference voltage Vclp) transferred to the vertical transfer line 339 and the noise-eliminated signal is transferred to the horizontal transfer line 258.

The drive pulse φR and drive pulse φX supplied to the reference voltage generating unit 356 are directly supplied from the timing generating unit 25 without going through the vertical scanning unit 241, and thus an index for selecting a row is not attached, and whichever row is being selected, the drive pulse φR and drive pulse φX are supplied to the reference voltage generating unit 356.

As described above, in this modified example of the first embodiment, by transferring, instead of a signal upon horizontal resetting, the reference voltage that has passed through the route like that of a normal imaging signal to the horizontal transfer line 258, a signal including a noise component that is mixed while the signal is being transferred from the unit pixel 230 is able to be transferred to the horizontal transfer line 258.

Figure 8:
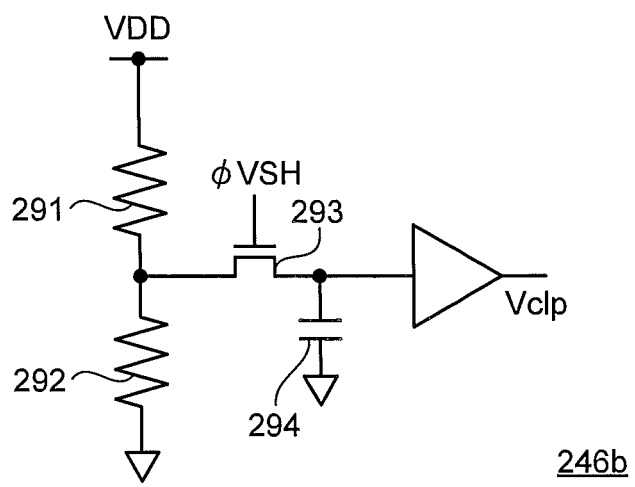
FIG. 8 is a circuit diagram illustrating a configuration of a reference voltage generating unit of the endoscope system according to the modified example of the first embodiment.

FIG. 8 is a circuit diagram illustrating a configuration of the reference voltage generating unit of the light receiving unit of the endoscope system according to the modified example of the first embodiment. A reference voltage generating unit 246b includes a resistance voltage dividing circuit formed of two resistances 291 and 292, a switch (transistor) 293 driven by the drive signal φVSH, and a capacitor (condenser) 294. The reference voltage generating unit 246b, at the timing of the drive signal φVSH, generates the clamp voltage Vclp of the noise eliminating unit 243 from the power supply voltage VDD that is the same as that of the light receiving unit 23. In this modified example, because the voltage generated in the reference voltage generating unit 356, instead of the reference voltage Vref, is transmitted to the connector unit 5, the reference voltage generating unit 246b outputs only the clamp voltage Vclp without outputting the reference voltage Vref. The rest of the configuration is similar to that of the reference voltage generating unit 246 according to the first embodiment.

Figure 9:
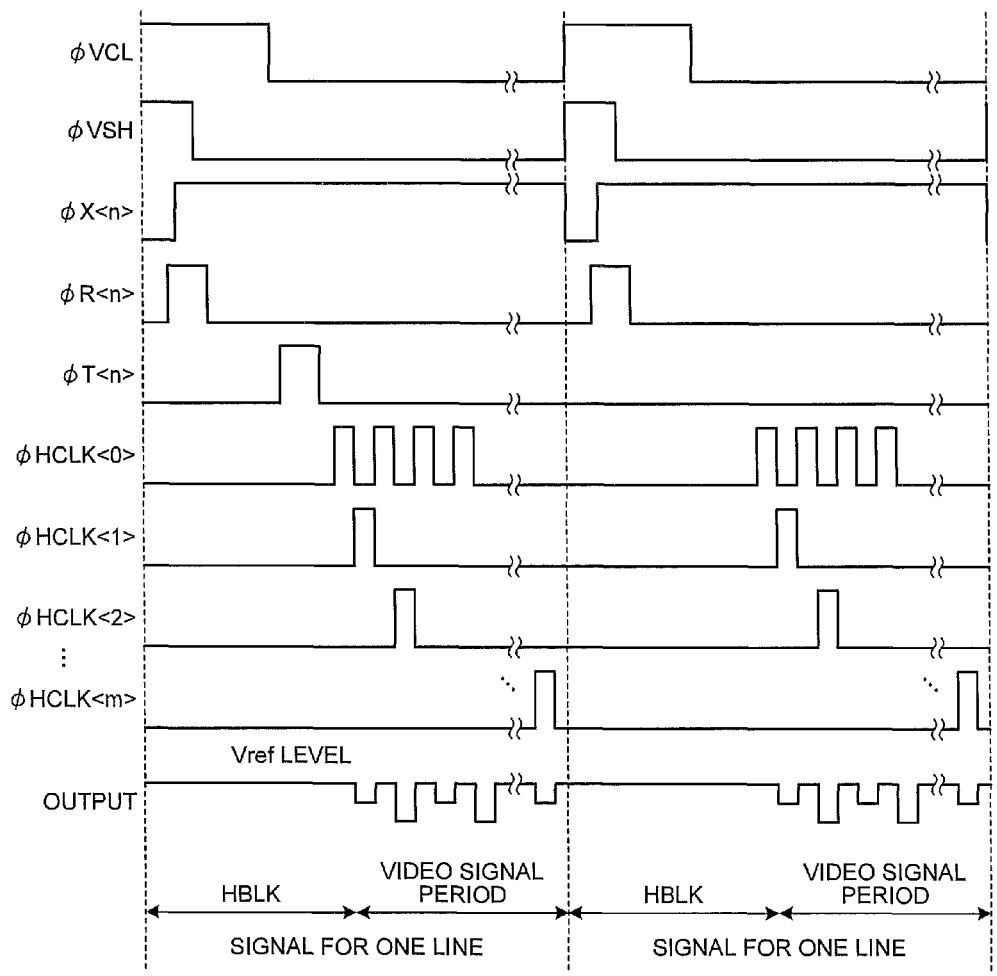
FIG. 9 is a timing chart illustrating driving signals of an imaging device according to the modified example of the first embodiment.

FIG. 9 is a timing chart illustrating driving signals of an imaging device according to the modified example of the first embodiment. First, the clamp switch 253 is turned ON (φVCL is High), the pixel output switch 238 is turned ON (φX<n> is High), the charge converter resetting unit 236 is turned ON (the drive pulse φR<n> is High), and the transfer transistors 234 and 235 are turned OFF (the drive pulse φT<n> is Low), to thereby output a noise signal including variation particular to the unit pixel 230 of row <n> and noise upon pixel resetting from the unit pixel 230 to the vertical transfer line 239. When that is done, because the output switch 338 of the reference voltage generating unit 356 is also turned ON (φX is High) and the resetting unit 336 is also turned ON (the drive pulse φR is High), the reference voltage is output to the vertical transfer line 339 from the reference voltage generating unit 356 also. Further, by keeping the clamp switch 253 in the ON state (φVCL is High), the gate of the column source follower transistor 244 is set to a voltage of the clamp voltage Vclp. The clamp voltage Vclp is determined at a falling timing of φVSH and the reference voltage Vref is also determined at this timing.

Next, by turning the transfer transistor 234 ON (the drive pulse φTa<n> is High) while the clamp switch 253 is in the OFF state (φVCL is Low), the charge photoelectrically converted by the photoelectric conversion element 231 is read out to the charge converter 233. When that is done, since the pixel output switch 238 is still ON (φX<n> is High), the imaging signal subjected to the voltage conversion is transferred to the vertical transfer line 239. By this operation, via the transfer capacitor 252, an imaging signal, from which a noise signal has been subtracted, is output to the gate of the column source follower transistor 244. The signal output to the gate of the column source follower transistor 244 is a signal sampled with reference to the clamp voltage Vclp.

By turning a column selection switch 354 of column <0> corresponding to the reference voltage generating unit 356 ON (the drive pulse φHCLK<0> is High) after sampling the imaging signal with reference to the clamp voltage Vclp, the reference voltage (clamp voltage Vclp) output by the reference voltage generating unit 356 is transferred to the horizontal transfer line 258. Thereafter, the column selection switch 354 of column <0> is turned OFF (drive pulse φHCLK<O> is Low) and the column selection switch 254 of column <1> is turned ON (drive pulse φHCLK<1> is High), to thereby transfer the imaging signal to the horizontal transfer line 258. Further, thereafter, the column selection switch 254 of column <1> is turned OFF (the drive pulse φHCLK<1> is Low) and the column selection switch 354 of column <0> corresponding to the reference voltage generating unit 356 is turned ON (the drive pulse φHCLK<O> is High) again, to thereby transfer the reference voltage (noise signal) output by the reference voltage generating unit 356 to the horizontal transfer line 258. Next, the column selection switch 354 of column <0> is turned OFF (the drive pulse φHCLK<O> is Low) and the column selection switch 254 of column <2> is turned ON (the drive pulse φHCLK<2> is High), to thereby transfer the imaging signal of the next column to the horizontal transfer line 258. By repeating such an operation as many times as the number of columns of the light receiving unit 23 (or the number of columns required to be read out), the reference voltage and the imaging signal (the imaging-signal-reference-voltage sum signal obtained by adding together the imaging signal and the reference voltage) output by the reference voltage generating unit 356 are output alternately from the output unit 31.

As described above, according to the modified example of the first embodiment of the present invention, similarly to the first embodiment, since the noise eliminating unit 243 does not require a condenser for sampling (a sampling capacitor), the capacity of the transfer capacitor (AC coupling condenser) 252 is able to be suppressed low. Further, since there is no sampling capacitor, an area occupied by the noise eliminating unit 243 is able to be reduced.

Further, according to the modified example of the first embodiment of the present invention, the reference voltage (clamp voltage Vclp) and the imaging signal output by the reference voltage generating unit 356 for each pixel are able to be output alternately. Thereby, for example, in a correlated double sampling circuit or the like provided in the connector unit 5, in-phase noise superimposed during transmission of a signal is able to be removed effectively. Further, the reference voltage, which is output by the reference voltage generating unit 356, goes through the route similar to that of the imaging signal and thus includes the noise component during the transfer, and the fluctuation of the ground GND is able to be transmitted to the connector unit 5 and the noise is able to be eliminated even more effectively than in the first embodiment.

In the above described modified example of the first embodiment, although a unit cell is formed of a single photoelectric conversion element without pixel sharing, a unit cell may be formed of a pair of two photoelectric conversion elements adjacent to each other in the column direction, similarly to the first embodiment. Further, a unit cell may be formed of a pair of two photoelectric conversion elements adjacent to each other in the row direction, or a unit cell may be formed of a set of four photoelectric conversion elements adjacent to one another in the row direction and column direction.

Second Embodiment

Figure 10:
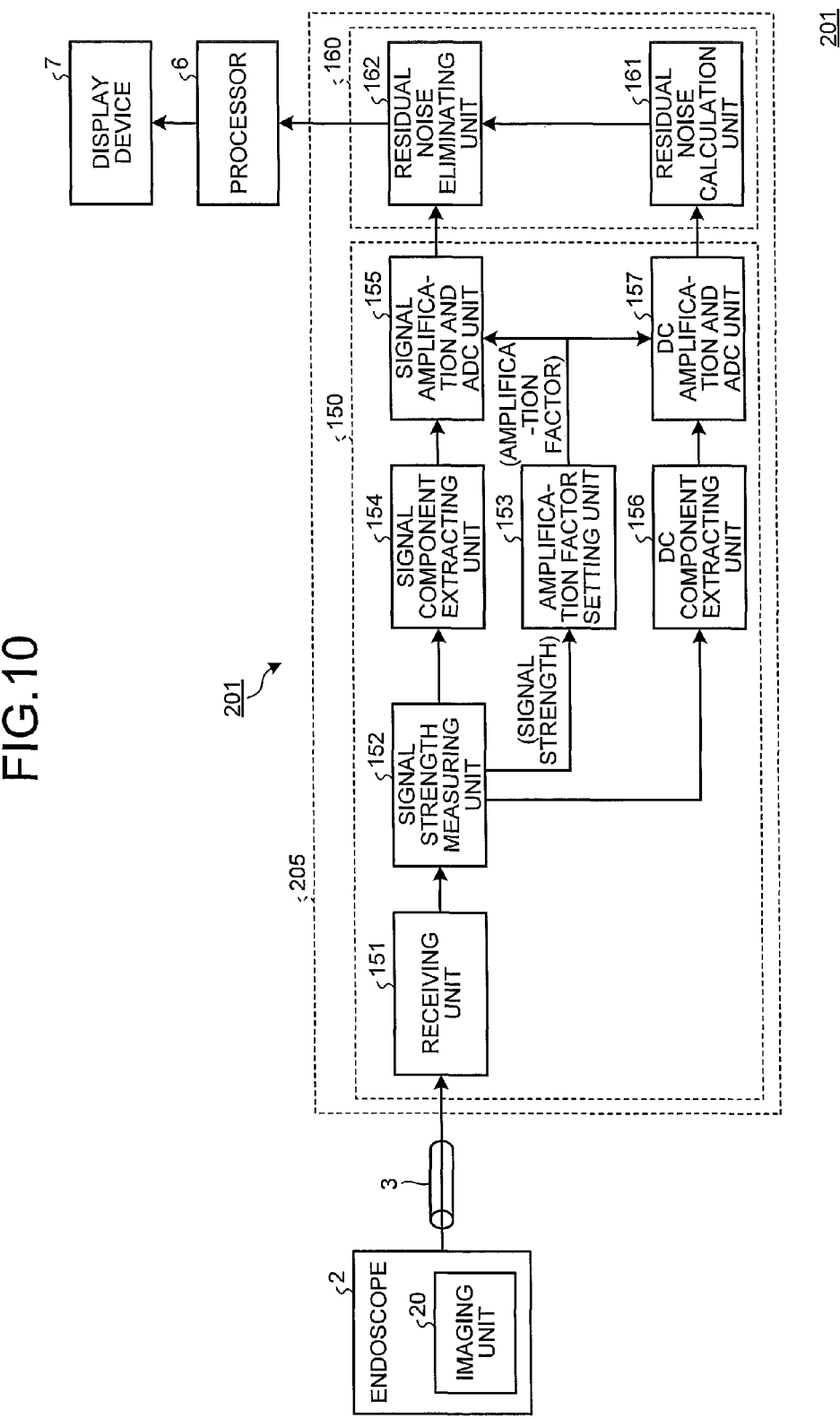
FIG. 10 is a block diagram illustrating functions of an endoscope system according to a second embodiment.

FIG. 10 is a block diagram illustrating functions of an endoscope system according to a second embodiment. In describing the endoscope system according to this second embodiment, to structural elements that are the same as those of the endoscope system according to the first embodiment, the same reference signs will be appended and detailed description thereof will be omitted.

An endoscope system 201 according to the second embodiment includes: an imaging unit 20 (hereinafter, simply referred to as "endoscope 2"), which outputs the imaging signal and the reference voltage (constant voltage signal) alternately and which is in the endoscope 2; a connector unit 205, which performs predetermined signal processing on the imaging signal output by the endoscope 2 and eliminates residual noise from the imaging signal based on the reference voltage output by the endoscope 2; a processor (control device) 6, which performs predetermined image processing on the image signal output from the connector unit 205 and controls the whole endoscope system 201; and a display device 7, which displays the image signal processed by the processor 6.

The connector unit 205 includes: an analog front end (AFE) unit 150, which receives and performs signal amplification and analog-digital conversion on the imaging signal and the reference voltage output by the endoscope 2; and an imaging signal processing unit 160 that performs a residual noise eliminating process on the digitalized signal.

The AFE unit 150 includes a receiving unit 151, a signal strength measuring unit 152, an amplification factor setting unit 153, a signal component extracting unit 154, a signal amplification and analog-digital conversion (ADC) unit 155, a direct current (DC) component extracting unit 156, and a DC amplification and analog-digital conversion (ADC) unit 157.

The receiving unit 151 receives an output signal (the imaging signal and the reference voltage) of the endoscope 2 and outputs the received signal to the signal strength measuring unit 152. The imaging signal and the reference voltage, which are received by the receiving unit 151, also include transmission system noise superimposed during transmission by the transmission cable 3 or the like and an in-phase noise component such as system power supply noise.

The signal strength measuring unit 152 measures a signal strength of the incoming output signal of the endoscope 2. Thereafter, the output signal is output to the signal component extracting unit 154 and the direct current (DC) component extracting unit 156. The signal strength measured by the signal strength measuring unit 152 is sent to the amplification factor setting unit 153, and the amplification factor setting unit 153 calculates an attenuation factor of the output signal of the endoscope 2 based on the signal strength measured and sets an amplification factor according to the attenuation factor.

The signal component extracting unit 154 extracts, from the signal input, only a signal component corresponding to the imaging signal, and outputs the signal component to the signal amplification and ADC unit 155. For example, the signal component extracting unit 154 performs a noise eliminating process by a correlated double sampling process or the like with the imaging signal and reference voltage that are alternately input, subtracts a reference voltage component from the imaging signal, and eliminates the in-phase noise component in transmission. However, the in-phase noise worth an elimination ratio of a common mode remains. This remaining in-phase noise component in transmission is called "residual noise component". The signal amplification and ADC unit 155 amplifies the signal component with the amplification factor set by the amplification factor setting unit 153, performs analog-digital conversion on the amplified signal component to output a digital imaging signal to a later described residual noise eliminating unit 162 of the imaging signal processing unit 160. The imaging signal amplified by the signal amplification and ADC unit 155 includes the residual noise component.

The DC component extracting unit 156 extracts, from the signal input, only a direct current component of the reference voltage. The DC component extracting unit 156 detects an in-phase component, such as the transmission system noise and system power supply noise, as level fluctuation, by taking in only the direct current component from the reference voltage. The level fluctuation of the in-phase noise component detected herein is output to the DC amplification and analog-digital conversion (ADC) unit 157, amplified with an amplification factor that is the same as that of the signal component, thereafter subjected to analog-digital conversion, and output to a later described residual noise calculation unit 161 of the imaging signal processing unit 160. By amplifying the in-phase noise component also by the amplification factor that is the same as that of the signal component, the residual noise component that increases according to the amplification factor of the signal component is able to be eliminated effectively.

Figure 11:
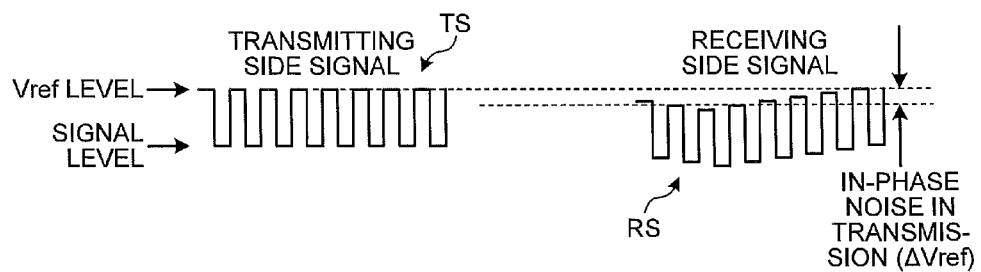
FIG. 11 is a conceptual diagram for illustrating an in-phase noise component in transmission in the second embodiment.

FIG. 11 is a conceptual diagram for illustrating an in-phase noise component in transmission in the second embodiment. A waveform TS at a transmitting side represents time variation of signal levels of the imaging signal and reference voltage Vref transmitted from the endoscope 2, and a waveform RS at a receiving side represents time variation of signal levels of the imaging signal and reference voltage Vref received by the receiving unit 151 of FIG. 10. Although the signal level of the imaging signal is always fluctuating actually, for convenience of explanation, in FIG. 11, the signal level of the imaging signal is illustrated as maintaining a constant level, and only the variation in the reference voltage Vref is focused herein.

As illustrated in FIG. 11, the signal level of the reference voltage Vref maintains a predetermined level like the waveform TS upon transmission, but by being transmitted over a long distance via the transmission cable 3, the in-phase noise in the transmission is superimposed, and like the waveform RS, in-phase level fluctuation occurs in the imaging signal and reference voltage. Such a noise component due to the in-phase level fluctuation of the imaging signal and reference voltage is eliminated by the correlated double sampling process in the signal component extracting unit 154, but the signal after this elimination still includes the residual noise component that increases according to the amplification factor of the signal component.

Therefore, in the second embodiment, by extracting the direct current component of the reference voltage, the level fluctuation of the in-phase noise component is extracted, and based on the extracted level fluctuation, the in-phase noise component that has remained after the correlated double sampling process is eliminated from the signal component. According to this embodiment, for example, for each reference voltage, a difference from a predetermined level is calculated, and an average value of the differences calculated for one line is used as the in-phase noise component ($\Delta$Vref) in order to eliminate the remaining in-phase noise component. The in-phase noise component is not limited to the average value for the one line, and may be a maximum value, a median value, or the like thereof.

Returning to FIG. 10, the description will be continued. The imaging signal processing unit 160, for example, is formed of a field programmable gate array (FPGA), and includes the residual noise calculation unit 161 and the residual noise eliminating unit 162. The residual noise calculation unit 161 calculates the residual noise component remaining in the imaging signal amplified in the signal amplification and ADC unit 155, based on the amplified in-phase noise component input from the DC amplification and ADC unit 157.

The residual noise component is calculated by, for example, first calculating the difference from the predetermined level for each reference voltage, multiplying the in-phase noise component ($\Delta$Vref), which is the average value of the differences calculated for one line of the pixel rows, by the amplification factor of the signal component, and performing division by a common mode removal ratio (CMRR) ($\Delta$Vref× signal component amplification factor/CMRR). The residual noise component found by the calculation is output to the residual noise eliminating unit 162.

The residual noise eliminating unit 162 eliminates the residual noise component by subtracting the residual noise component calculated by the residual noise calculation unit 161, from the digital imaging signal amplified by the signal amplification and ADC unit 155. Thereafter, the digital imaging signal, from which the residual noise component has been eliminated, is output to the processor 6. Similarly to the first embodiment, the processor 6 performs predetermined image processing or the like on the digital imaging signal and outputs, as an image signal, the image-processed digital imaging signal to the display device 7.

The display device 7 displays an image based on the image signal.

Figure 12:
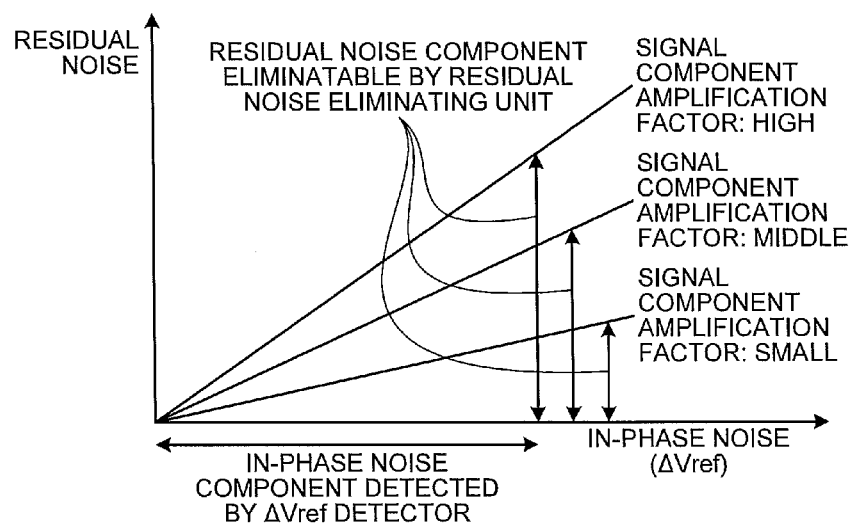
FIG. 12 is a graph for illustrating a transmission noise eliminating effect according to the second embodiment.

FIG. 12 is a graph for illustrating a transmission noise eliminating effect according to the second embodiment. In FIG. 12, a vertical axis represents residual noise level, and a horizontal axis represents level of the in-phase noise ($\Delta$Vref) detected by the residual noise calculation unit 161. When the amplification factor of the signal component changes, the in-phase noise level also changes following that change, and since the residual noise calculation unit 161 multiplies the detected in-phase noise ($\Delta$Vref) by the amplification factor of the signal component, according to the amplification factor of the signal component, the residual noise component is able to be eliminated. If the amplification factor of the signal component is high, the level of the residual noise component eliminated by the residual noise eliminating unit 162 also becomes high, and if the amplification factor of the signal component is low, the level of the residual noise component eliminated by the residual noise eliminating unit 162 also becomes low.

As described above, according to the second embodiment of the present invention, by extracting the direct current component of the reference voltage, the level fluctuation of the in-phase noise component is detected, and based on the detected level fluctuation, the in-phase noise component is able to be eliminated from the signal component. Further, by amplifying the detected in-phase noise component by the same amplification factor as the signal component, the in-phase noise component that has increased in level by the amplification is able to be eliminated effectively.

Third Embodiment

Figure 13:
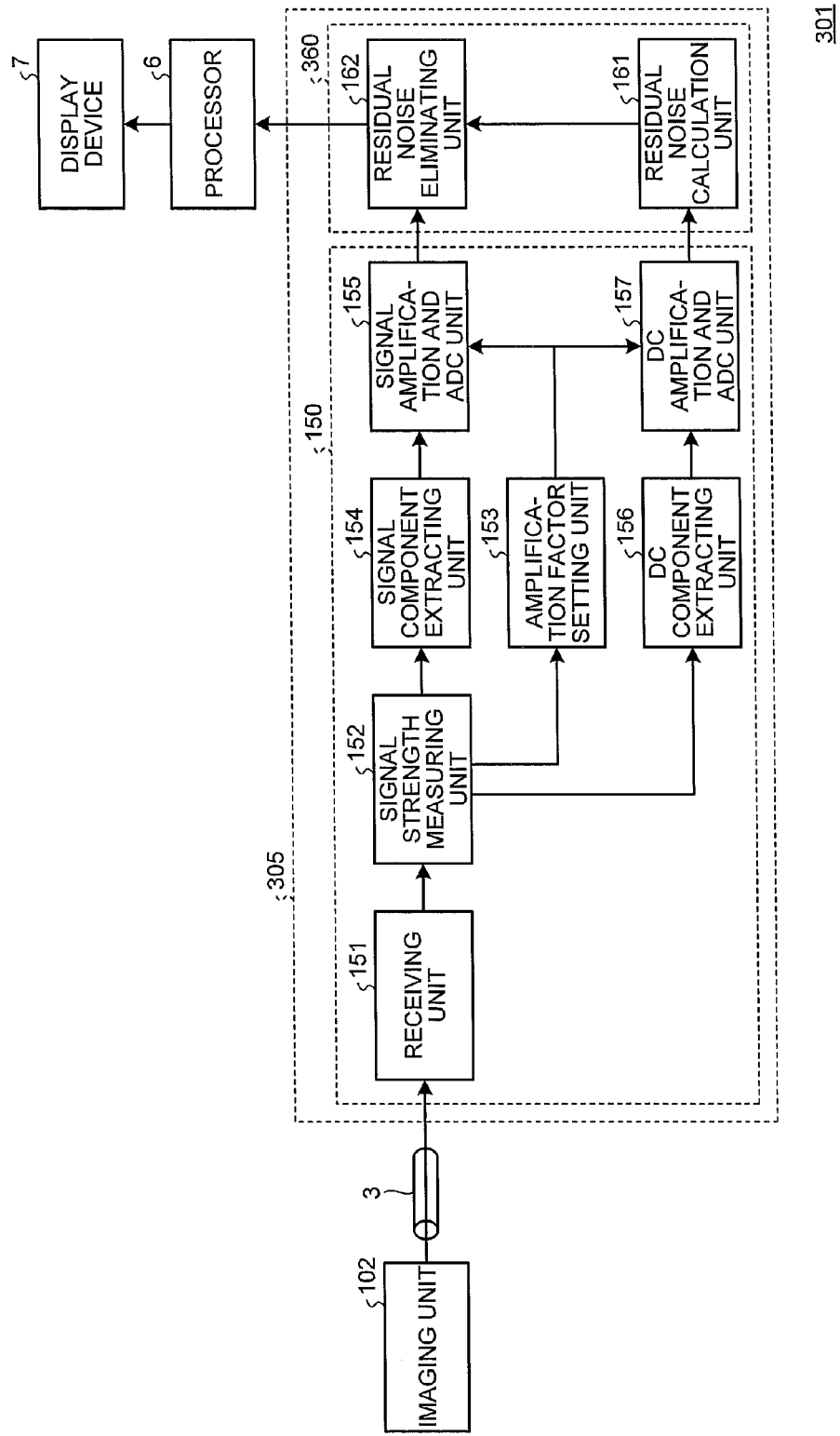
FIG. 13 is a block diagram illustrating functions of an endoscope system according to a third embodiment.

FIG. 13 is a block diagram illustrating functions of an endoscope system according to a third embodiment. In describing the endoscope system according to this third embodiment, to structural elements that are the same as those of the endoscope system according to the first embodiment or second embodiment, the same reference signs will be appended and detailed description thereof will be omitted.

An endoscope system 301 according to the third embodiment includes: an imaging unit (endoscope) 102, which alternately outputs an imaging signal and a reference signal (constant voltage signal); a connector unit 305, which performs predetermined signal processing on the imaging signal output by the imaging unit 102 and eliminates residual noise from the imaging signal, based on the reference signal output by the imaging unit 102; a processor (control device) 6, which performs predetermined image processing on the imaging signal output by the connector unit 305 and controls the whole endoscope system 301; and a display device 7, which displays the image signal processed by the processor 6.

The imaging unit 102 is an imaging device, which is able to alternately output the imaging signal and the reference signal. An image sensor of the imaging unit 102 may be an image sensor of any type, as long as the image sensor is able to output the imaging signal and the reference signal. In this third embodiment, a case, in which the imaging unit 102 is a CCD image sensor, will be described. The reference signal transmitted by the imaging unit 102 may be a reference voltage generated based on a power supply voltage particular to the imaging unit 102, or may be a reference voltage (power supply voltage reference signal) generated by the imaging unit 102 based on a power supply voltage supplied from the processor 6 or connector unit 305 to the imaging unit 102.

Similarly to the second embodiment, the connector unit 305 includes: an analog front end (AFE) unit 150, which receives the imaging signal and reference signal (clamp signal) output by the imaging unit 102 and performs signal amplification and analog-digital conversion; and an imaging signal processing unit 360 that performs a residual noise eliminating process on the digitalized signal.

The AFE unit 150 is approximately the same as that of the second embodiment, and includes a receiving unit 151, a signal strength measuring unit 152, an amplification factor setting unit 153, a signal component extracting unit 154, a signal amplification and analog-digital conversion (ADC) unit 155, a direct current (DC) component extracting unit 156, and a DC amplification and analog-digital conversion (ADC) unit 157.

The imaging signal processing unit 360, for example, is formed of a field programmable gate array (FPGA) and includes a residual noise calculation unit 161 and a residual noise eliminating unit 162, which have functions similar to those of the second embodiment. The rest of the configuration is similar to that of the second embodiment, and an imaging signal received by the receiving unit 151 is subjected to elimination of a residual noise component, output as an image signal to the processor 6, and displayed as an image by the display device 7.

Figure 14:
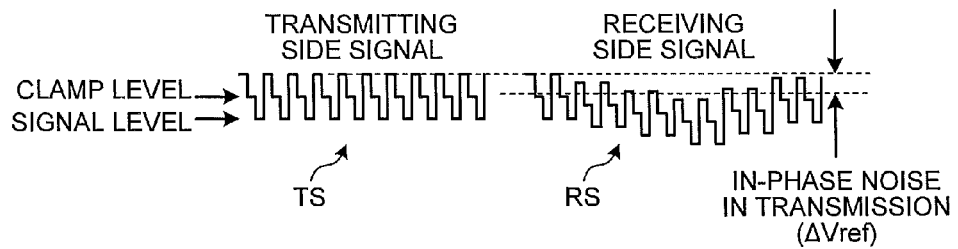
FIG. 14 is a conceptual diagram for illustrating an in-phase noise component in transmission in the third embodiment.
Figure 15:
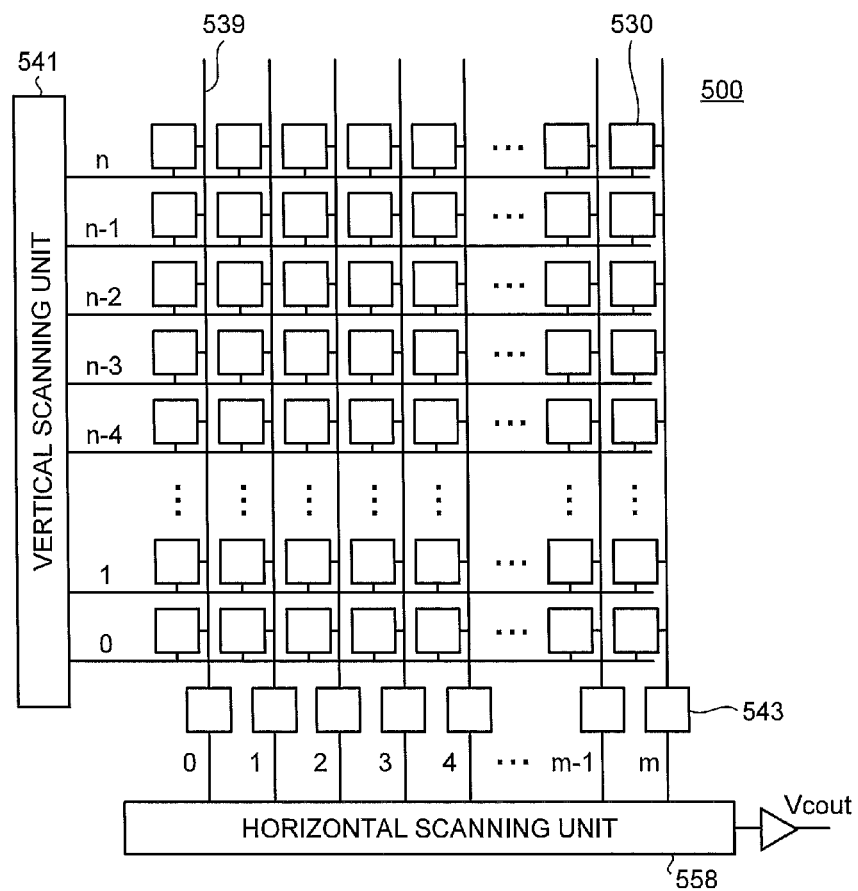
FIG. 15 is a circuit diagram illustrating a configuration of a conventional imaging device.
Figure 16:
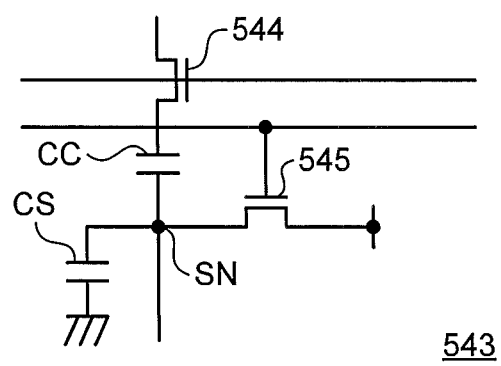
FIG. 16 is a circuit diagram illustrating a configuration of a noise eliminating unit of the imaging device illustrated in FIG. 15.

FIG. 14 is a conceptual diagram for illustrating an in-phase noise component in transmission in the third embodiment. A waveform TS represents time variation of signal levels of the imaging signal and reference signal transmitted from the imaging unit 102 having the CCD image sensor, and a waveform RS represents time variation of signal levels of the imaging signal and reference signal received by the receiving unit 151 of FIG. 13. In the CCD image sensor, since clamping is performed with a median value of a ternary waveform, a clamp level becomes the reference signal. Therefore, in the third embodiment, the clamp level is used as the reference signal. Although the signal level of the imaging signal is always fluctuating actually, for convenience of explanation, in FIG. 14, the signal level of the imaging signal is illustrated as maintaining a constant level, and only the variation in the reference signal (Vref) is focused herein.

As illustrated in FIG. 14, the signal level of the reference signal maintains a predetermined level in the transmission, but by being transmitted over a long distance via the transmission cable 3, the in-phase noise in the transmission is superimposed and as illustrated on the right side of FIG. 14, in-phase level fluctuation occurs in the imaging signal and reference signal.

Accordingly, in the third embodiment too, similarly to the second embodiment, by extracting a direct current component of the reference signal, the level fluctuation of the in-phase noise component is extracted, and based on the extracted level fluctuation, the residual in-phase noise component is eliminated from the signal component. According to this embodiment, for example, for each reference signal, a difference from a predetermined level is calculated, and an average value of the differences calculated for one line of pixel rows is used as an in-phase noise component ($\Delta Vref$) in order to eliminate the in-phase noise component. The in-phase noise component is not limited to the average value for the one line, and may be a maximum value, a median value, or the like thereof. A technique and configuration for eliminating the in-phase noise component remaining in the imaging signal are similar to those of the second embodiment.

As described above, similarly to the second embodiment, according to the third embodiment, by extracting the direct current component of the reference signal, the level fluctuation of the in-phase noise component is detected, and based on the detected level variation, the in-phase noise component is able to be eliminated from the signal component. Further, by amplifying the detected in-phase noise component by the amplification factor that is the same as the signal component, the in-phase noise component that has increased in level by the amplification is able to be eliminated effectively.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

(Note 1)

An endoscope system, in which an imaging device that outputs an imaging signal, and an image signal processing apparatus, which processes the imaging signal and generates an image signal, are connected to each other, wherein
  the imaging device comprises:
    an imaging unit that images a subject;
    an imaging control unit that controls the imaging unit to output a reference signal of the imaging unit, and a sum signal obtained by adding together an imaging signal and the reference signal; and
    an imaging device communication unit that transmits the reference signal and the sum signal to the image signal processing apparatus, and
  the image signal processing apparatus comprises:
    an image processing apparatus communication unit that receives, from the imaging device, the reference signal and the sum signal;
    a measuring unit that measures signal strengths of the reference signal and sum signal received by the image processing apparatus communication unit;
    an amplification factor setting unit that sets, based on the signal strengths measured by the measuring unit, a signal amplification factor;

an imaging signal calculation unit that performs calculation, based on the set signal amplification factor, on the reference signal and the sum signal and outputs an imaging signal; and an image signal processing unit that generates, based on the imaging signal output by the imaging signal calculation unit, an image signal.

(Note 2)

The endoscope system according to Note 1, wherein the image signal processing apparatus further comprises a power supply unit that supplies a power supply voltage to the imaging device, and the imaging device further comprises:

a power supply voltage reference signal generating unit that generates a power supply voltage reference signal based on the power supply voltage supplied from the power supply unit; and a power supply voltage reference signal transmitting unit that transmits the power supply voltage reference signal as the reference signal.

What is claimed is:

1. An imaging device, comprising:
a photoelectric conversion element that performs photoelectric conversion according to an amount of light received and accumulates a charge;
a first transfer unit that transfers the accumulated charge;
a charge converter that converts the transferred charge to a voltage or current signal;
a charge converter resetting unit that resets the charge converter to a first voltage;
a signal output unit that outputs the converted signal;
a first transfer line connected to the signal output unit;
a transfer capacitor connected to the first transfer line;
a second transfer unit that is connected to the first transfer line via the transfer capacitor and to which a signal is output from the first transfer line due to coupling by a capacity of the transfer capacitor;
a transfer capacitor resetting unit that resets the transfer capacitor to a second voltage;
a second transfer line to which a signal from the second transfer unit is output;
a drive unit that causes a signal to be output from the first transfer line via the second transfer unit by a noise signal reading operation and a light-noise sum signal reading operation, the noise signal reading operation resetting the transfer capacitor by the transfer capacitor resetting unit when the signal of the charge converter is output to the first transfer line via the signal output unit after the first transfer unit is turned into an OFF state and the charge converter is reset by the charge converter resetting unit, and the light-noise sum signal reading operation outputting the signal of the charge converter to the first transfer line via the signal output unit after the transfer capacitor resetting unit is turned into an OFF state, the first transfer unit is turned into an ON state, and the charge accumulated by the photoelectric conversion element is transferred;
a reference voltage generating unit that generates a reference voltage having a fluctuation component in phase with the second voltage; and
an output selector that is connected to the second transfer line and the reference voltage generating unit, and selects and outputs a signal input from the second transfer line and the reference voltage input from the reference voltage generating unit.

2. The imaging device according to claim 1, further comprising:
a second transfer line resetting unit that resets the second transfer line to a third voltage; and
a sampling and holding unit that is provided between the second transfer line and the output selector,
wherein the light-noise sum signal reading operation inputs only the signal output from the first transfer line to the output selector by repeating: resetting the second transfer line after sampling the signal output from the first transfer line by the sampling and holding unit when the signal of the first transfer line is output to the second transfer line.

3. An imaging device, comprising:
a photoelectric conversion element that performs photoelectric conversion according to an amount of light received and accumulates a charge;
a first transfer unit that transfers the accumulated charge;
a charge converter that converts the transferred charge to a voltage or current signal;
a charge converter resetting unit that resets the charge converter to a first voltage;
a signal output unit that outputs the converted signal;
a first transfer line connected to the signal output unit;
a transfer capacitor connected to the first transfer line;
a second transfer unit that is connected to the first transfer line via the transfer capacitor and to which a signal is output from the first transfer line due to coupling by a capacity of the transfer capacitor;
a transfer capacitor resetting unit that resets the transfer capacitor to a second voltage;
a second transfer line to which a signal from the second transfer unit is output;
a reference voltage generating unit that generates a reference voltage based on the first voltage and comprises a reference voltage generating unit resetting unit that resets a voltage of the reference voltage generating unit to the first voltage, a reference voltage generating unit signal output unit that outputs a signal of the reference voltage generating unit resetting unit, and a third transfer unit that outputs, as the reference voltage, a signal from the reference voltage generating unit signal output unit to the second transfer line; and
a drive unit that causes a signal to be output from the first transfer line via the second transfer unit by a noise signal reading operation and a light-noise sum signal reading operation, and drives the second transfer unit and the third transfer unit such that the signal output from the first transfer line and the reference voltage are alternately output to the second transfer line, the noise signal reading operation resetting the transfer capacitor by the transfer capacitor resetting unit when the signal of the charge converter is output to the first transfer line via the signal output unit after the first transfer unit is turned into an OFF state and the charge converter is reset by the charge converter resetting unit, and the light-noise sum signal reading operation outputting the signal of the charge converter to the first transfer line via the signal output unit after the transfer capacitor resetting unit is turned into an OFF state, the first transfer unit is turned into an ON state, and the charge accumulated by the photoelectric conversion element is transferred.

4. An endoscope system comprising:
an imaging device, comprising:
a photoelectric conversion element that performs photoelectric conversion according to an amount of light received and accumulates a charge;

a first transfer unit that transfers the accumulated charge;
a charge converter that converts the transferred charge to a voltage or current signal;
a charge converter resetting unit that resets the charge converter to a first voltage;
a signal output unit that outputs the converted signal;
a second transfer unit that is connected to a first transfer line connected to the signal output unit, a transfer capacitor connected to the first transfer line, and the first transfer line via the transfer capacitor, the second transfer unit to which a signal is output from the first transfer line by coupling due to a capacity of the transfer capacitor;
a transfer capacitor resetting unit that resets the transfer capacitor to a second voltage;
a second transfer line to which a signal from the second transfer unit is output;
a drive unit that causes a signal to be output from the first transfer line via the second transfer unit by a noise signal reading operation and a light-noise sum signal reading operation, the noise signal reading operation resetting the transfer capacitor by the transfer capacitor resetting unit when the signal of the charge converter is output to the first transfer line via the signal output unit after the first transfer unit is turned into an OFF state and the charge converter is reset by the charge converter resetting unit, and the light-noise sum signal reading operation outputting the signal of the charge converter to the first transfer line via the signal output unit after the transfer capacitor resetting unit is turned into an OFF state, the first transfer unit is turned into an ON state, and the charge accumulated by the photoelectric conversion element is transferred; and
an output selector that is connected to: a reference voltage generating unit that generates a reference voltage having a fluctuation component in phase with the second voltage; the second transfer line; and the reference voltage generating unit, and selects and outputs a signal input from the second transfer line and the reference voltage input from the reference voltage generating unit;
a transmitting unit that transmits the signal output from the first transfer line and the reference voltage that are output by the imaging device;
a receiving unit that receives the signal transmitted by the transmitting unit; and
a calculation unit that performs calculation on the signal received by the receiving unit.

5. The endoscope system according to claim 4, wherein the calculation unit includes:
a signal strength measuring unit that measures a signal strength of the signal received by the receiving unit;
an amplification factor setting units that sets, based on the measured signal strength, an amplification factor of the signal received by the receiving unit; and
an imaging signal calculation unit that performs calculation, based on the amplification factor and the reference voltage, on the signal output from the first transfer line and the reference voltage, and outputs an imaging signal obtained by subtracting an in-phase noise component in transmission from the signal output from the first transfer line.

6. The endoscope system according to claim 5, wherein the imaging signal calculation unit includes:
a direct current component extracting unit that extracts a direct current component of the reference voltage; and
a noise component eliminating unit that eliminates, based on the amplification factor and the direct current component, the in-phase noise component in transmission included in the signal output from the first transfer line.

7. An endoscope system comprising:
an imaging device, comprising:
a photoelectric conversion element that performs photoelectric conversion according to an amount of light received and accumulates a charge;
a first transfer unit that transfers the accumulated charge;
a charge converter that converts the transferred charge to a voltage or current signal;
a charge converter resetting unit that resets the charge converter to a first voltage;
a signal output unit that outputs the converted signal;
a first transfer line connected to the signal output unit;
a second transfer unit that is connected to a transfer capacitor connector to the first transfer line and the first transfer line via the transfer capacitor and to which a signal is output from the first transfer line due to coupling by a capacity of the transfer capacitor;
a transfer capacitor resetting unit that resets the transfer capacitor to a second voltage;
a second transfer line to which a signal from the second transfer unit is output;
a reference voltage generating unit that generates a reference voltage based on the first voltage and comprises a reference voltage generating unit resetting unit that resets a voltage of the reference voltage generating unit to the first voltage, a reference voltage generating unit signal output unit that outputs a signal of the reference voltage generating unit resetting unit, and a third transfer unit that outputs, as the reference voltage, the signal from the reference voltage generating unit signal output unit to the second transfer line; and
a drive unit that causes a signal to be output from the first transfer line via the second transfer unit by a noise signal reading operation and a light-noise sum signal reading operation, and drives the second transfer unit and the third transfer unit such that the signal output from the first transfer line and the reference voltage are alternately output to the second transfer line, the noise signal reading operation resetting the transfer capacitor by the transfer capacitor resetting unit when the signal of the charge converter is output to the first transfer line via the signal output unit after the first transfer unit is turned into an OFF state and the charge converter is reset by the charge converter resetting unit, and the light-noise sum signal reading operation outputting the signal of the charge converter to the first transfer line via the signal output unit after the transfer capacitor resetting unit is turned into an OFF state, the first transfer unit is turned into an ON state, and the charge accumulated by the photoelectric conversion element is transferred;
a transmitting unit that transmits the signal output from the first transfer line and the reference voltage that are output by the imaging device;
a receiving unit that receives the signal transmitted by the transmitting unit; and
a calculation unit that performs calculation on the signal received by the receiving unit.

8. The endoscope system according to claim 7, wherein the calculation unit includes:
a signal strength measuring unit that measures a signal strength of the signal received by the receiving unit;

an amplification factor setting units that sets, based on the measured signal strength, an amplification factor of the signal received by the receiving unit; and an imaging signal calculation unit that performs calculation, based on the amplification factor and the reference voltage, on the signal output from the first transfer line and the reference voltage, and outputs an imaging signal obtained by subtracting an in-phase noise component in transmission from the signal output from the first transfer line.

9. The endoscope system according to claim 8, wherein the imaging signal calculation unit includes:

a direct current component extracting unit that extracts a direct current component of the reference voltage; and a noise component eliminating unit that eliminates, based on the amplification factor and the direct current component, the in-phase noise component in transmission included in the signal output from the first transfer line.

10. A method of eliminating noise in an imaging device, which comprises: a photoelectric conversion element that performs photoelectric conversion according to an amount of light received and accumulates a charge; a first transfer unit that transfers the accumulated charge; a charge converter that converts the transferred charge to a voltage or current signal; a charge converter resetting unit that resets the charge converter to a first voltage; a signal output unit that outputs the converted signal; a first transfer line connected to the signal output unit; a transfer capacitor connected to the first transfer line; a second transfer unit that is connected to the first transfer line via the transfer capacitor and to which a signal is output from the first transfer line due to coupling by a capacity of the transfer capacitor; a transfer capacitor resetting unit that resets the transfer capacitor to a second voltage; and a second transfer line to which a signal from the second transfer unit is output, the method including:

turning the first transfer unit into an OFF state and resetting the charge converter by the charge converter resetting unit;

resetting the transfer capacitor by the transfer capacitor resetting unit when the signal of the charge converter is output to the first transfer line via the signal output unit;

turning the transfer capacitor resetting unit into an OFF state, turning the first transfer unit into an ON state, and transferring the charge accumulated by the photoelectric conversion element;

outputting the signal of the charge converter to the first transfer line via the signal output unit;

causing a signal to be output from the first transfer line via the second transfer unit;

reference voltage generation of generating a reference voltage having a fluctuation component in phase with the second voltage; and output and selection of selecting and outputting a signal input from the second transfer line and the reference voltage generated in the reference voltage generation.

11. A method of eliminating noise in an imaging device, which comprises: a photoelectric conversion element that performs photoelectric conversion according to an amount of light received and accumulates a charge; a first transfer unit that transfers the accumulated charge; a charge converter that converts the transferred charge to a voltage or current signal; a charge converter resetting unit that resets the charge converter to a first voltage; a signal output unit that outputs the converted signal; a first transfer line connected to the signal output unit; a transfer capacitor connected to the first transfer line; a second transfer unit that is connected to the first transfer line via the transfer capacitor and to which a signal is output from the first transfer line due to coupling by a capacity of the transfer capacitor; a transfer capacitor resetting unit that resets the transfer capacitor to a second voltage; a second transfer line to which a signal from the second transfer unit is output; and a reference voltage generating unit that generates a reference voltage based on the first voltage and comprises a reference voltage generating unit resetting unit that resets a voltage of the reference voltage generating unit to the first voltage, a reference voltage generating unit signal output unit that outputs a signal of the reference voltage generating unit resetting unit, and a third transfer unit that outputs, as the reference voltage, a signal from the reference voltage generating unit signal output unit to the second transfer line, the method including:

turning the first transfer unit into an OFF state and resetting the charge converter by the charge converter resetting unit;

resetting the transfer capacitor by the transfer capacitor resetting unit when the signal of the charge converter is output to the first transfer line via the signal output unit;

turning the transfer capacitor resetting unit into an OFF state, turning the first transfer unit into an ON state, and transferring the charge accumulated by the photoelectric conversion element;

outputting the signal of the charge converter to the first transfer line via the signal output unit; and driving the second transfer unit and the third transfer unit such that a signal output from the first transfer line and the reference voltage are alternately output to the second transfer line.

* * * * *